US 9,244,037 B2

(12) United States Patent
Fujiwara et al.

(10) Patent No.: US 9,244,037 B2
(45) Date of Patent: Jan. 26, 2016

(54) METHOD FOR MEASURING HEMATOCRIT VALUE OF BLOOD SAMPLE, METHOD FOR MEASURING CONCENTRATION OF ANALYTE IN BLOOD SAMPLE, SENSOR CHIP AND SENSOR UNIT

(71) Applicant: Panasonic Corporation, Kadoma-shi, Osaka (JP)

(72) Inventors: Masaki Fujiwara, Ehime (JP); Shin Ikeda, Ehime (JP); Takahiro Nakaminami, Osaka (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 278 days.

(21) Appl. No.: 13/845,907

(22) Filed: Mar. 18, 2013

(65) Prior Publication Data

US 2014/0116879 A1     May 1, 2014

Related U.S. Application Data

(63) Continuation of application No. 12/377,514, filed as application No. PCT/JP2007/070290 on Oct. 17, 2007, now Pat. No. 8,691,072.

(30) Foreign Application Priority Data

Oct. 19, 2006   (JP) .................................. 2006-285027
Oct. 19, 2006   (JP) .................................. 2006-285028

(51) Int. Cl.
  *G01N 27/327*   (2006.01)
  *G01N 27/413*   (2006.01)

(52) U.S. Cl.
  CPC .......... *G01N 27/413* (2013.01); *G01N 27/3274* (2013.01)

(58) Field of Classification Search
  CPC ..................................... G01N 27/327–27/3274
  USPC .............. 204/403.01–403.15; 205/777.5–778
  See application file for complete search history.

(56) References Cited

U.S. PATENT DOCUMENTS

| | | | |
|---|---|---|---|
| 4,835,477 A | | 5/1989 | Polaschegg et al. |
| 5,385,846 A | * | 1/1995 | Kuhn et al. ................ 205/777.5 |
| 5,906,921 A | | 5/1999 | Ikeda et al. |
| 6,287,451 B1 | | 9/2001 | Winarta et al. |
| 2001/0006149 A1 | | 7/2001 | Taniike et al. |

(Continued)

FOREIGN PATENT DOCUMENTS

| | | |
|---|---|---|
| EP | 0 417 796 | 3/1991 |
| EP | 1 447 665 | 8/2004 |
| JP | 1-026157 | 1/1989 |
| JP | 3-099254 | 4/1991 |
| JP | 8-500190 | 1/1996 |
| JP | 11-101771 | 4/1999 |
| JP | 11-118794 | 4/1999 |
| JP | 2003-501627 | 1/2003 |
| JP | 2004-069582 | 3/2004 |
| WO | 01/57510 | 8/2001 |
| WO | 2005/040407 | 5/2005 |
| WO | 2005/054839 | 6/2005 |
| WO | 2005/054840 | 6/2005 |
| WO | 2005/103669 | 11/2005 |
| WO | WO2005103669 | * 11/2005 |

*Primary Examiner* — Bach Dinh
(74) *Attorney, Agent, or Firm* — Hamre, Schumann, Mueller & Larson, P.C.

(57) ABSTRACT

Provided is a sensor chip for electrochemically measuring a concentration of an analyte in a blood sample. In one embodiment of the sensor, the sensor chip includes a substrate, and a preliminary measurement analyzer and a hematocrit value analyzer disposed on the substrate. The preliminary measurement analyzer includes a preliminary working electrode and a preliminary counter electrode. The hematocrit value analyzer includes a working electrode and a counter electrode. An oxidant of a redox substance is disposed on the preliminary measurement analyzer and the counter electrode. A reductant of a redox substance is disposed on the working electrode.

4 Claims, 38 Drawing Sheets

(56) References Cited

U.S. PATENT DOCUMENTS

| | | |
|---|---|---|
| 2002/0048532 A1 | 4/2002 | Lin et al. |
| 2004/0194302 A1* | 10/2004 | Bhullar et al. ......... C12Q 1/001 29/847 |
| 2007/0062822 A1 | 3/2007 | Fujiwara et al. |
| 2007/0080073 A1 | 4/2007 | Wu et al. |
| 2007/0131565 A1 | 6/2007 | Fujiwara et al. |
| 2007/0138026 A1* | 6/2007 | Fujiwara et al. ........... 205/777.5 |

\* cited by examiner (A)

(B)

(A)

(B)

(A)

(B)

(A)

(B)

METHOD FOR MEASURING HEMATOCRIT VALUE OF BLOOD SAMPLE, METHOD FOR MEASURING CONCENTRATION OF ANALYTE IN BLOOD SAMPLE, SENSOR CHIP AND SENSOR UNIT

TECHNICAL FIELD

The present invention relates to a method for measuring a hematocrit (Hct) value of a blood sample, a method for measuring a concentration of an analyte in a blood sample, and a sensor chip and a sensor unit suited for such measurements.

BACKGROUND ART

Sensor chips have been used for the measurement of an analyte concentration in a blood sample, for example, such as a blood glucose concentration (blood sugar level).

The sensor chip measures the amount of current flowing in the blood sample after an enzymatic cycling reaction involving an analyte, and a concentration of the analyte is calculated based on the measured current amount. The amount of current varies not only with the analyte concentration but the Hct value of the blood sample. The Hct value of the blood sample varies according to the physical condition of the animal from which the blood sample is drawn. In humans, the Hct value is normally 39% to 50% for adult males, and 36% to 45% for adult females. It is therefore desirable that the Hct value of the blood sample also be measured by the sensor chip in order to specify accurately the analyte concentration in the blood sample, and to find the attributes of the blood sample, for example, such as blood viscosity and anemia.

Sensor chips for measuring the Hct value of a blood sample are disclosed in JP8 (1996)-500190T, JP15 (2003)-501627T, a pamphlet of International Publication 2005/054839, and a pamphlet of International Publication 2005/054840. These known sensor chips include an electrode system equipped with a working electrode and a counter electrode, and a channel (blood sample holder) for holding a blood sample between the working electrode and counter electrode.

In the sensor chip of the JP8 (1996)-500190T, a reductant and an oxidant of an electron mediator are disposed on the blood sample holder to be dissolved by a blood sample. The reductant and the oxidant of the electron mediator mix with the blood sample introduced into the blood sample holder, and adhere to the working and counter electrodes in the mixture with the blood sample. In the sensor chip described in JP15 (2003)-501627T, the oxidant of the electron mediator is disposed on the working and counter electrodes. In these sensor chips, the Hct value of the blood sample is specified by measuring the amount of current that flows in the blood sample as a result of a redox reaction of the electron mediator adhering to the electrodes.

In the sensor chips described in the pamphlet of International Publication 2005/054839 and the pamphlet of International Publication 2005/054840, the electron mediator is disposed only on the counter electrode of the electrode system including the working and counter electrodes for measuring a Hct value. In these sensor chips, a pure blood sample not containing the electron mediator contacts the working electrode following introduction of the blood sample into the blood sample holder. In the sensor chips, movement of electrons occurs at the interface of the blood sample and the working electrode as a result of a redox reaction of the blood components in the blood sample, for example, such as ascorbic acid, uric acid, and water. The electron mediator disposed on the counter electrode is involved in the movement of electrons at the interface of the blood sample and the counter electrode.

DISCLOSURE OF THE INVENTION

In the sensor chips described in JP8 (1996)-500190T and JP15 (2003)-501627T, the amount of current (redox current) that flows in the blood sample in the measurement of Hct value varies only slightly with respect to a rate of change of the Hct value of the blood sample. Accordingly, the detection sensitivity is not sufficient in these sensor chips. For example, in some cases, a change in amplitude of the redox current is only about 8% when a change in Hct value of the blood sample is 20%. In the sensor chips described in the pamphlet of International Publication 2005/054839 and the pamphlet of International Publication 2005/054840, the amplitude of the redox current fluctuates over a wide range when the voltage (Hct value measuring voltage) applied across the working electrode and the counter electrode in the measurement of Hct value is decreased. A stable Hct measurement in the blood sample would not be possible in this case.

An object of the present invention is to provide a method for measuring a Hct value of a blood sample, a method for measuring a concentration of an analyte in a blood sample, and a sensor chip and a sensor unit suited for such measurements, that are capable of stably measuring the Hct value of the blood sample with sufficient detection sensitivity even at a low Hct value measuring voltage.

The inventors of the present invention designed such a layout pattern of the redox substance disposed on a sensor chip that, following introduction of a blood sample, a reductant of the redox substance is in contact with the working electrode and an oxidant of the redox substance is contact with the counter electrode while the other form of the redox substance is substantially not in contact with the counter electrode or the working electrode. The inventors found that, with such a layout pattern, the amplitude fluctuations of the redox current can be suppressed and the rate of amplitude change of the redox current with respect to a change in Hct value immediately after the voltage application can be increased, even when the voltage applied across the working electrode, serving as the anode, and the counter electrode, serving as the cathode, is decreased.

The present invention provides a method for electrochemically measuring a Hct value of a blood sample. The method includes: applying a voltage across a working and a counter electrode in contact with the blood sample; detecting a resulting current flowing between the working electrode and the counter electrode; and calculating a Hct value of the blood sample based on the current. The voltage is applied across the working electrode and the counter electrode while an oxidant of a redox substance is in contact with the counter electrode and substantially not in contact with the working electrode, and a reductant of the redox substance in contact with the working electrode and substantially not in contact with the counter electrode. The current is detected by measuring a current that results from the oxidation of the reductant and the reduction of the oxidant caused by the voltage application.

In another aspect, the present invention provides a method for electrochemically measuring a concentration of an analyte in a blood sample. The method includes: electrochemically detecting a current A reflecting a Hct value of the blood sample so as to obtain data A representing the current A or an equivalent of the current A and corresponding to the Hct value; electrochemically detecting a current B that results from the oxidation or reduction of the analyte in the blood sample caused, in the presence of a redox substance, by a redox enzyme that uses the analyte as a substrate, so as to obtain data B representing the current B or an equivalent of the current B; and determining a concentration of the analyte in the blood sample based on data C obtained by correcting the data B using the data A. The current A is detected by detecting a current that results from the oxidation of a reductant and the reduction of an oxidant of the redox substance caused by application of a voltage across a working electrode and a counter electrode. The voltage is applied while the oxidant of the redox substance is in contact with the counter electrode and substantially not in contact with the working electrode, and the reductant of the redox substance is in contact with the working electrode and substantially not in contact with the counter electrode.

In another aspect, the present invention provides a sensor chip including a Hct value analyzer that electrochemically detects a current reflecting a Hct value of a blood sample. The Hct value analyzer includes: a working electrode and a counter electrode; a blood sample holder for holding the blood sample in contact with the working electrode and the counter electrode; and a blood sample inlet through which the blood sample is introduced into the blood sample holder. A first reagent containing an oxidant of a redox substance and substantially not containing a reductant of the redox substance is disposed to cover a surface of the counter electrode facing the blood sample holder. A second reagent containing the reductant and substantially not containing the oxidant is disposed to cover a surface of the working electrode facing the blood sample holder. In another aspect, the present invention discloses a sensor chip including a Hct value analyzer that electrochemically detects a current reflecting a Hct value of a blood sample. The Hct value analyzer includes: a working electrode and a counter electrode; a blood sample holder for holding the blood sample in contact with the working electrode and the counter electrode; and a blood sample inlet through which the blood sample is introduced into the blood sample holder. The blood sample holder includes an inlet portion in communication with the blood sample inlet; and a first and a second branch portion branching out of the inlet portion. The first branch portion faces the counter electrode, and the second branch portion faces the working electrode. A first reagent containing an oxidant of a redox substance and substantially not containing a reductant of the redox substance is disposed on the first branch portion. A second reagent containing the reductant and substantially not containing the oxidant is disposed on the second branch portion. In another aspect, the present invention provides a sensor chip including a Hct value analyzer that electrochemically detects a current reflecting a Hct value of a blood sample. The Hct value analyzer includes: a working electrode and a counter electrode; a blood sample holder for holding the blood sample in contact with the working electrode and the counter electrode; and a blood sample inlet through which the blood sample is introduced into the blood sample holder. The blood sample holder includes a first reagent, disposed on the blood sample holder, containing an oxidant of a redox substance and substantially not containing a reductant of the redox substance, and a second reagent, disposed on the blood sample holder, containing the reductant and substantially not containing the oxidant. One of the first reagent and the second reagent is disposed on the upstream side of the other reagent with respect to a flow of the blood sample introduced into the blood sample holder through the blood sample inlet. (a) When the other reagent is the first reagent, the counter electrode is disposed on the downstream side of the working electrode with respect to the flow of the blood sample, and the first reagent is disposed to cover a surface of the counter electrode facing the blood sample holder, the working electrode is disposed on the upstream side of the counter electrode with respect to the flow of the blood sample, and the second reagent is disposed separately from the working electrode on the upstream side of the working electrode with respect to the flow of the blood sample, or disposed in contact with the working electrode. (b) When the other reagent is the second reagent, the working electrode is disposed on the downstream side of the counter electrode with respect to the flow of the blood sample, and the second reagent is disposed to cover a surface of the working electrode facing the blood sample holder, the counter electrode is disposed on the upstream side of the working electrode with respect to the flow of the blood sample, and the second reagent is separately disposed from the counter electrode on the upstream side of the counter electrode with respect to the flow of the blood sample, or disposed in contact with the counter electrode.

Further, in another aspect, the present invention provides a sensor unit including the sensor chip, and a sensor main body including a voltage applying circuit for applying a predetermined voltage across the working electrode and the counter electrode. The sensor chip is detachable with respect to the sensor main body, and the voltage applying circuit is capable of applying a predetermined voltage across the working electrode and the counter electrode with the sensor chip attached to the sensor main body. The predetermined voltage is 3.0 V or less, when the working electrode is anode and the counter electrode is cathode.

According to the present invention, the Hct value of the blood sample stably can be measured with sufficient detection sensitivity, even at a low Hct value measuring voltage.

BEST MODE FOR CARRYING OUT THE INVENTION

Figure 1:
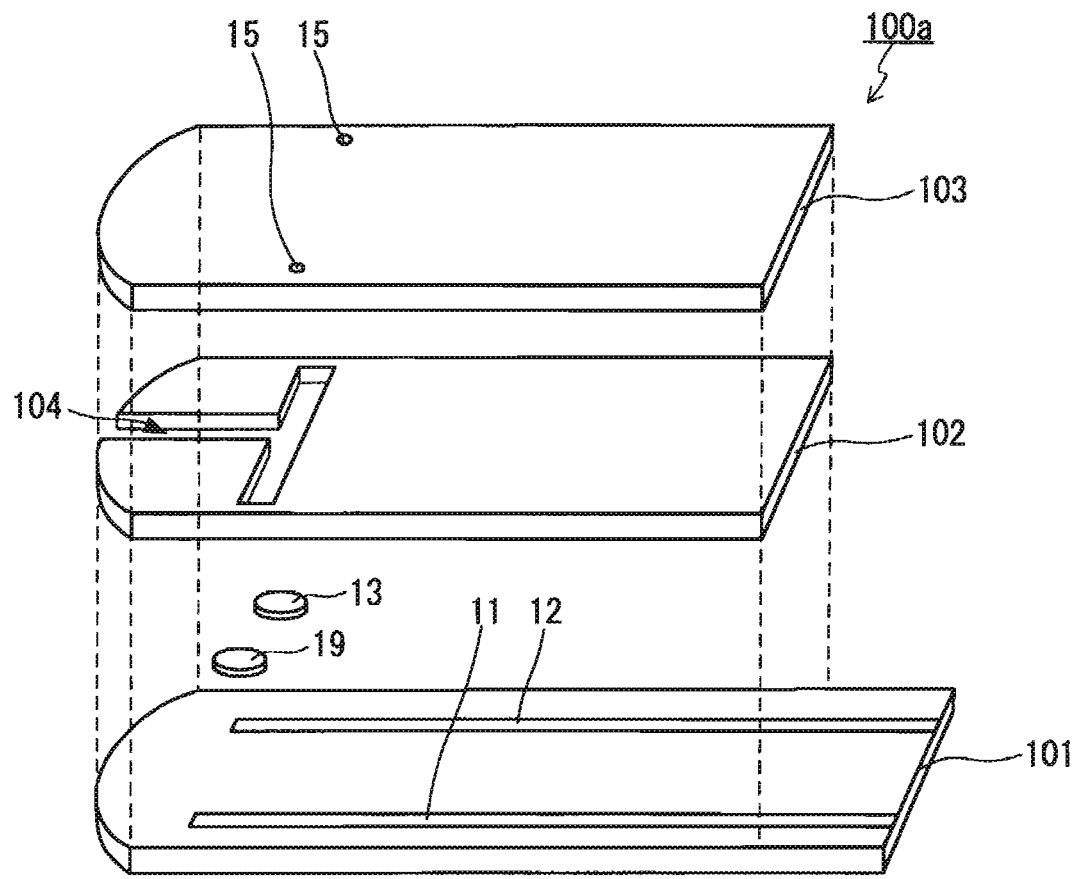
FIG. 1 is an exploded perspective view showing an example of a sensor chip for measuring a Hct value of the present invention.

In a measurement of Hct value by the present invention, the contact pattern of a redox substance and electrodes is controlled such that the oxidant of the redox substance is substantially not in contact with a working electrode but in contact with a counter electrode, and that the reductant of the redox substance is substantially not in contact with the counter electrode but is in contact with the working electrode.

The oxidant or the reductant of the redox substance being in contact with the counter electrode or working electrode may be a state in which, for example, a blood sample containing the redox substance is in contact with the electrodes, or a state in which, for example, the redox substance is disposed on the electrodes or embedded in the surfaces of the electrodes. That is, in the measurement of Hct value, the redox substance may be in contact with the electrodes by being dissolved in the blood sample, or by being provided as a solid.

The reductant is a substance that undergoes electrochemical oxidation at the working electrode in response to an applied voltage of 3.0 V or less, when the working electrode is the anode and the counter electrode is the cathode. Examples of the reductant include reductants of reversible electroactive compounds such as ferrocyanides, p-hydroquinone, p-hydroquinone derivative, reduced phenazine methosulfate, leucomethylene blue, ferrocene, and ferrocene derivative. Other examples are ascorbic acid, uric acid, acetaminophen, silver, copper, and nickel, among others. Preferably, the reductant is a ferrocyanide, which is preferably potassium ferrocyanide.

The oxidant is a substance that undergoes electrochemical reduction at the counter electrode in response to an applied voltage of 3.0 V or less, when the working electrode is the anode and the counter electrode is the cathode. Examples of the oxidant include oxidants of reversible electroactive compounds such as ferricyanides, p-benzoquinone, p-benzoquinone derivative, oxidized phenazine methosulfate, methylene blue, ferricinium, and ferricinium derivative. The oxidant is preferably a ferricyanide, which is preferably potassium ferricyanide.

The amount of redox substance in contact with the electrodes (wording electrode and counter electrode) in the measurement of Hct value may be controlled by adding, for example, a 0.1 to 1000 mM, 1 to 500 mM, or in some cases, 10 to 200 mM oxidant and reductant to the blood sample brought into contact with the electrodes.

In the measurement of Hct value, the redox substance intrinsically contained in the blood sample (for example, human blood) is disregarded as the redox substance in contact with the electrodes (working electrode and counter electrode). In other words, in this specification, the redox substance intrinsically contained in the blood sample is regarded as being substantially not in contact with the electrodes. Further, in this specification, a blood sample containing the redox substance in an amount comparable to that intrinsically contained in human blood is regarded as being substantially not containing the redox substance.

The oxidant or the reductant substantially not being in contact with the electrodes may be a state in which the surface of the electrode is covered with a reagent substantially not containing the oxidant or the reductant. For example, a reagent substantially not containing the reductant may be disposed to cover the surface of the counter electrode to realize a state in which the reductant is substantially not in contact with the counter electrode, even when the blood sample contains the reductant.

The material of the working electrode is preferably a conducting material, for example, such as palladium, platinum, gold, titanium, or carbon, that does not readily undergo oxidation when a voltage of 3.0 V or less is applied to the working electrode, when the working electrode is the anode and the counter electrode is the cathode. With the working electrode made of such a conducting material, the Hct value of the blood sample can be measured more stably. The working electrode may be, for example, an electrode core made of a conducting material exemplified above, or may include, for example, a polymer film formed on the electrode core. Examples of the material of the polymer film include: carboxymethyl cellulose; hydroxyethyl cellulose; hydroxypropyl cellulose; methyl cellulose; ethyl cellulose; ethylhydroxyethyl cellulose; carboxyethyl cellulose; polyvinyl alcohol; polyvinyl pyrrolidone; polyamino acid such as polylysine; polystyrene sulfonate; gelatin and a derivative thereof polyacrylic acid and a salt thereof, polymethacrylic acid and a salt thereof starch and a derivative thereof maleic anhydride polymer and a salt thereof and agarose gel and a derivative thereof. These compounds may be used either individually or in a combination of two or more kinds.

A conducting material used for the counter electrode is not particularly limited. The counter electrode may be, for example, an electrode core made of a known conducting material as represented by the examples given above, or may include, for example, the polymer film formed on the electrode core.

The shape and size of the working electrode and counter electrode are not particularly limited. The layout pattern of the working electrode and counter electrode on an insulating substrate is not particularly limited either. However, a stable measurement of Hct value in a blood sample would be possible when the closest distance between the working electrode and the counter electrode is 0.05 mm or greater, 0.1 mm or greater, or in some cases, 0.5 mm or greater. The upper limit of the closest distance is not particularly limited.

In the measurement of Hct value, a voltage of 3.0 V or less is applied across the working electrode and the counter electrode (Hct value measuring voltage), when the working electrode is the anode and the counter electrode is the cathode. In the present invention, the application of the Hct value measuring voltage across the working electrode and the counter electrode as the anode and the cathode, respectively, stably can produce a current associated with the oxidation of the reductant in contact with the working electrode and the reduction of the oxidant in contact with the counter electrode, immediately after the voltage application, even when the applied voltage is 3.0 V or less, or even 1.0 V or less. Though the reason for this is unclear, it appears to be due to the oxidation current that occurs solely by the oxidation reaction of the reductant in contact with the working electrode, and the gradual formation of an oxide film on the surface of the working electrode, in the measurement of Hct value.

The Hct value measuring voltage is applied for, for example, 0.001 to 60 seconds, preferably 0.01 to 10 seconds, more preferably 0.01 to 5 seconds, and even more preferably 0.01 to 3 seconds. The Hct value measuring voltage may be, for example, 0.75 V or less, 0.5 V or less, 0.25 V or less, 0.15 V or less, or 0.1 V or less, when the working electrode is the anode and the counter electrode is the cathode. The lower limit of the Hct value measuring voltage is not particularly limited as long as the reductant is oxidized at the working electrode and the oxidant is reduced at the counter electrode. However, it is desirable that the Hct value measuring voltage exceed 0 V and create a positive potential at the working electrode, when the working electrode is the anode and the counter electrode is the cathode.

The Hct value of the blood sample is calculated based on the current that flows between the working electrode and the counter electrode by the application of the Hct value measuring voltage. The Hct value can be calculated, for example, by referring to a standard curve or a standard table relating Hct value to the amount of current after a predetermined time period from the application of the Hct value measuring voltage.

The Hct value described above can be measured using a sensor chip for measuring a Hct value, which is an example of a sensor chip of the present invention.

The sensor chip for measuring a Hct value includes a Hct value analyzer, which electrochemically detects a current reflecting the Hct value of the blood sample. The Hct value analyzer includes an electrode system having the working electrode and the counter electrode, and a blood sample holder used to hold a blood sample in contact with the working electrode and the counter electrode. The blood sample holder is in communication with a blood sample inlet through which a blood sample is introduced.

The working electrode and the counter electrode are disposed to at least partially face the blood sample holder, such that the working electrode and the counter electrode are in contact with the blood sample introduced into the blood sample holder. The surfaces of the working electrode and the counter electrode facing the blood sample holder may be, for example, the surfaces of the electrode cores forming these electrodes, or, for example, the surfaces of the polymer films formed on the electrode cores. The electrode cores of the working electrode and the counter electrode can be formed, for example, by a screen printing method, a sputtering method, or a vapor-deposition method. The polymer film can be formed, for example, from a solution of polymer material for forming the film, by applying the solution on the electrode core and drying it. The shape and size of the working electrode and counter electrode, and the layout pattern of these electrodes on the insulating substrate are not particularly limited. However, the Hct value of the blood sample stably can be measured more easily when the closest distance between the working electrode and the counter electrode falls in the ranges exemplified above. In the Hct value analyzer, when a blood sample is introduced into the blood sample holder and a voltage is applied across the working electrode and the counter electrode, the blood sample should be in contact with the counter electrode and the working electrode such that the oxidant of the redox substance is substantially not in contact with the working electrode but in contact with the counter electrode, and that the reductant of the redox substance is substantially not in contact with the counter electrode but in contact with the working electrode. To this end, the layout pattern of the reagents containing the oxidant or the reductant of the redox substance, the shape of the blood sample holder, and the relative layout pattern of the counter electrode and the working electrode are set as follows.

(1) A first reagent containing the oxidant of the redox substance and substantially not containing the reductant of the redox substance is disposed to cover the surface of the counter electrode facing the blood sample holder, and a second reagent containing the reductant and substantially not containing the oxidant is disposed to cover the surface of the working electrode facing the blood sample holder. With this layout of the reagents covering the surfaces of the respective electrodes, the surface of each electrode will be in contact with only the intended form, either the oxidant or the reductant, of the redox substance and substantially not in contact with the redox substance of the other form in the measurement of Hct value, even when the redox substance in one of the reagents dissolves into the introduced blood sample and migrates with the blood sample to the area near the electrode on which the other reagent is disposed.

(2) When the blood sample holder includes an inlet portion in communication with the blood sample inlet, and a first and a second branch portion branching out of the inlet portion, and when the first branch portion faces the counter electrode and the second branch portion faces the working electrode, the first reagent and the second reagent may be disposed on the first branch portion and the second branch portion, respectively. With this layout, the surface of each electrode will be in contact with only the intended oxidant or reductant, and substantially not in contact with the redox substance of the other form as in the case of (1). At the branch portion, the reagent may be separated from the electrode, or in contact with the electrode.

(3) In the blood sample holder, one of the first reagent and the second reagent is disposed on the upstream side of the other reagent with respect to the flow of the blood sample introduced into the blood sample holder through the blood sample inlet. (a) When the other reagent is the first reagent, the counter electrode may be disposed on the downstream side of the working electrode with respect to the flow of the blood sample, and the first reagent may be disposed to cover the surface of the counter electrode facing the blood sample holder. The working electrode may be disposed on the upstream side of the counter electrode with respect to the flow of the blood sample, and the second reagent may be disposed separately from the working electrode on the upstream side of the working electrode with respect to the flow of the blood sample, or may be disposed in contact with the working electrode. (b) When the other reagent is the second reagent, the working electrode may be disposed on the downstream side of the counter electrode with respect to the flow of the blood sample, and the second reagent may be disposed to cover the surface of the working electrode facing the blood sample holder. The counter electrode may be disposed on the upstream side of the working electrode with respect to the flow of the blood sample, and the second reagent may be disposed separately from the counter electrode on the upstream side of the counter electrode with respect to the flow of the blood sample, or may be disposed in contact with the counter electrode. With this layout of the reagent covering the surface of the electrode disposed on the downstream side, the surface of each electrode will be in contact with only the intended form, either the oxidant or the reductant, of the redox substance and substantially not in contact with the redox substance of the other form in the measurement of Hct value, even when the redox substance in one of the reagents disposed on the upstream side of the downstream electrode dissolves into the introduced blood sample and migrates with the blood sample to the area near the downstream electrode on which the other reagent is disposed.

The reagent containing the redox substance (oxidant, reductant) further may include other compounds. Some of the examples of such additional compounds include: amino acids (homogenizer) such as taurine, glycine, serine, proline, threonine, and lycine; carboxymethyl cellulose; hydroxyethyl cellulose; hydroxypropyl cellulose; methyl cellulose; ethyl cellulose; ethylhydroxyethyl cellulose; carboxyethyl cellulose; polyvinyl alcohol; polyvinyl pyrrolidone; polyamino acid such as polylysine; polystyrene sulfonate; gelatin and a derivative thereof, polyacrylic acid and a salt thereof, polymethacrylic acid and a salt thereof, starch and a derivative thereof, maleic anhydride polymer and a salt thereof, and agarose gel. The amount of redox substance disposed in the Hct value analyzer may be set such that the amount of redox substance in contact with the electrodes in the measurement of Hct value is, for example, in a concentration of 0.1 to 1000 mM, 1 to 500 mM, or in some cases, 10 to 200 mM.

The shape and volume of the blood sample holder desirably are set such that the blood sample can be introduced therein by capillary action.

FIGS. 1 through 6, and FIGS. 28 and 29 are diagrams depicting specific examples of the layout pattern of the reagents containing the redox substance, the shape of the blood sample holder, and the relative layout pattern of the counter electrode and the working electrode, in the sensor chip for measuring a Hct value.

<Sensor Chip A for Measuring Hct Value>

Figure 2:
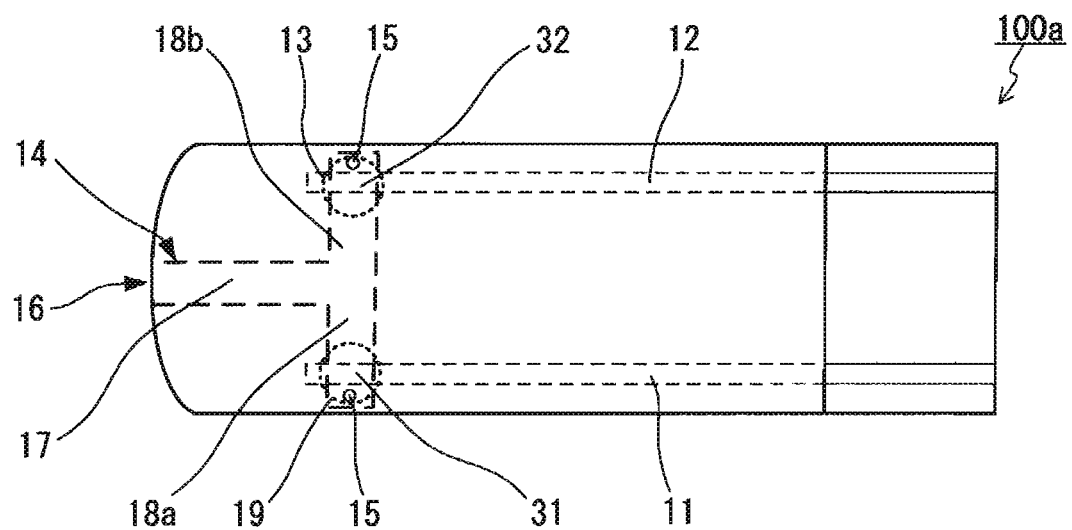
FIG. 2 is a plan view showing an example of a sensor chip for measuring a Hct value of the present invention.

FIG. 1 is an exploded perspective view of a sensor chip A for measuring a Hct value, and FIG. 2 is a plan view of the sensor chip shown in FIG. 1. As shown in the figures, a sensor chip A100a for measuring a Hct value includes a spacer 102 having a T-shaped cutout portion 104, an insulating substrate 101, and a cover 103. The cover 103 is disposed on the insulating substrate 101 with the spacer 102 in between, leaving one end portion of the insulating substrate 101 uncovered (on the right in the figures). These members 101, 102, and 103 are integrated, for example, by bonding or heat fusion. The cutout portion 104 of the spacer 102 serves as a blood sample holder 14 after integration of the members. The blood sample holder 14 includes an inlet portion 17 extending along the longer side of the chip 100a, and two branch portions 18a and 18b branching out of the inlet portion 17 and extending along the shorter side of the chip 100a.

The inlet portion 17 is in communication with the outside at an end portion of the spacer 102 (on the left in the figures). In other words, the blood sample holder 14 is in communication with a blood sample inlet 16 that opens to the outside of the chip 100a. The cover 103 includes outlets 15, respectively corresponding in position to the ends of the branch portions 18a and 18b. A working electrode 11 and a counter electrode 12 are disposed on the insulating substrate 101 such that a portion (portion 31) of the working electrode 11 and a portion (portion 32) of the counter electrode 12 face the branch portions 18a and 18b, respectively. The working electrode 11 and the counter electrode 12 each are connected to a lead (not shown). An end of each lead is exposed to outside of the chip 100a at the end portion of the insulating substrate 101 not covered with the spacer 102 and the cover 103, in order to apply a voltage across the working electrode and the counter electrode.

A first reagent 13 containing the oxidant of the redox substance and substantially not containing the reductant is disposed in contact with the portion 32 of the counter electrode 12. A second reagent 19 containing the reductant of the redox substance and substantially not containing the oxidant is disposed in contact with the portion 31 of the working electrode 11. These reagents may not easily dissolve into the blood sample or may dissolve easily into the blood sample.

Preferably, the first reagent 13 is disposed in contact with only the portion 32 of the counter electrode in the blood sample holder 14. By disposing the reagent this way, a pure blood sample substantially not containing the oxidant of the redox substance can be placed in a large quantity between the working electrode and the counter electrode in the measurement of Hct value. This improves the detection sensitivity of the Hct value.

The materials of the insulating substrate, the spacer, and the cover are not particularly limited as long as the working electrode and the counter electrode are not shorted by the integration. Examples of such materials include polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), methacrylic resin (PMMA), ABS resin (ABS), and glass.

In a sensor chip for measuring a Hct value of the present invention, one of the requirements in introducing a blood sample into the blood sample holder and applying a voltage across the working electrode and the counter electrode is that the blood sample is in contact with the counter electrode and the working electrode while the oxidant of the redox substance from the reagent disposed in the sensor chip is in contact with the counter electrode but substantially not in contact with the working electrode, and the reductant of the redox substance from the reagent disposed in the sensor chip is in contact with the working electrode but substantially not in contact with the counter electrode. So long as these conditions are met, any arrangement can be made concerning the layout pattern of the first and second reagents in the blood sample holder, the shape of the blood sample holder, the layout pattern of the reagents containing the redox substance, and the relative layout pattern of the counter electrode and the working electrode. Other exemplary configurations of a sensor chip for measuring a Hct value of the present invention are described below.

<Sensor Chip B for Measuring Hct Value>

Figure 28:
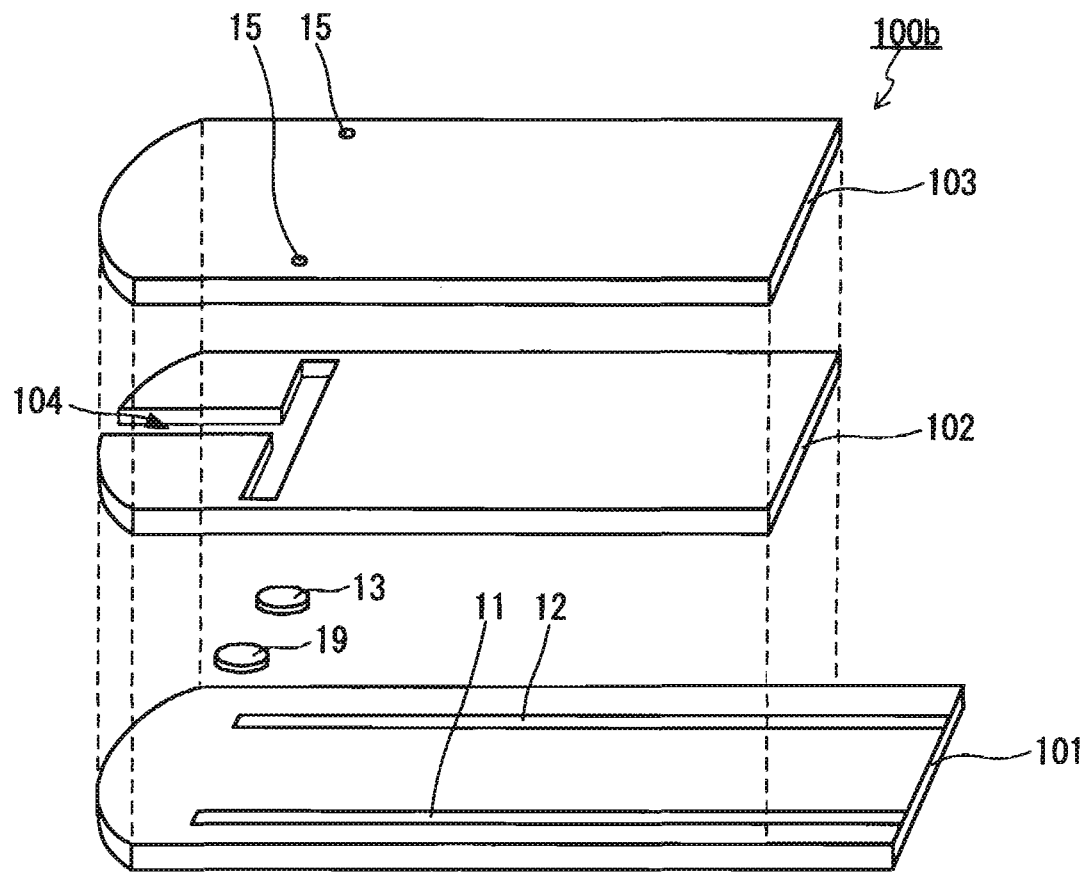
FIG. 28 is an exploded perspective view showing another example of a sensor chip for measuring a Hct value of the present invention.
Figure 29:
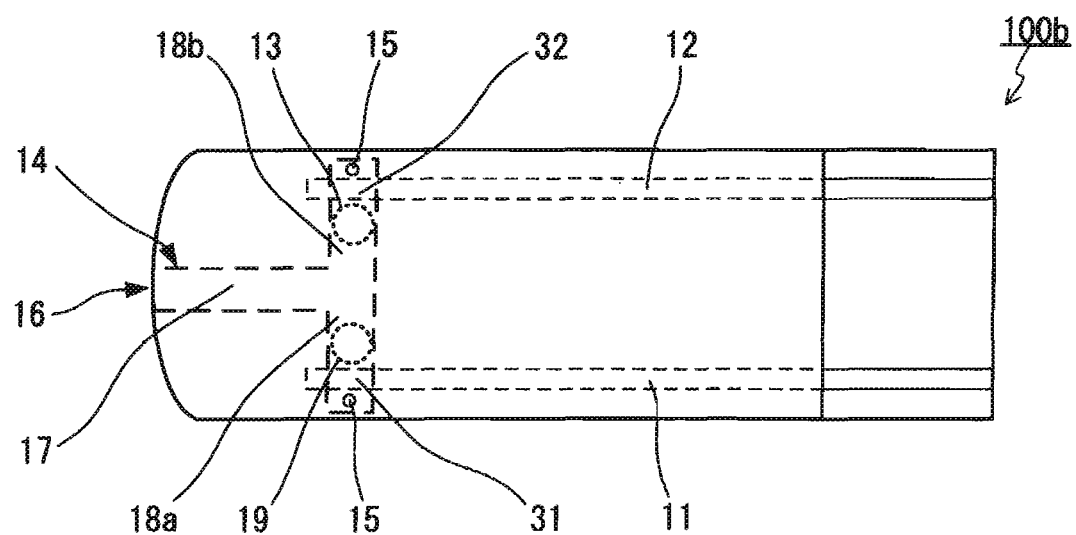
FIG. 29 is a plan view showing another example of a sensor chip for measuring a Hct value of the present invention.

FIG. 28 is an exploded perspective view of a sensor chip B for measuring a Hct value, and FIG. 29 is a plan view of the sensor chip shown in FIG. 28. As shown in the figures, a sensor chip B100b for measuring a Hct value has the same configuration as the sensor chip A for measuring a Hct value except that, at the branch portion 18a, the second reagent 19 is separated from the portion 31 of the working electrode 11 and is closer to the inlet portion 17 than the portion 31 is, and that, at the branch portion 18b, the first reagent 13 is separated from the portion 32 of the counter electrode 12 and is closer to the inlet portion 17 than the portion 32 is. The first reagent and the second reagent easily dissolve into the blood sample introduced into the branch portions 18a and 18b.

<Sensor Chip C for Measuring Hct Value>

Figure 3:
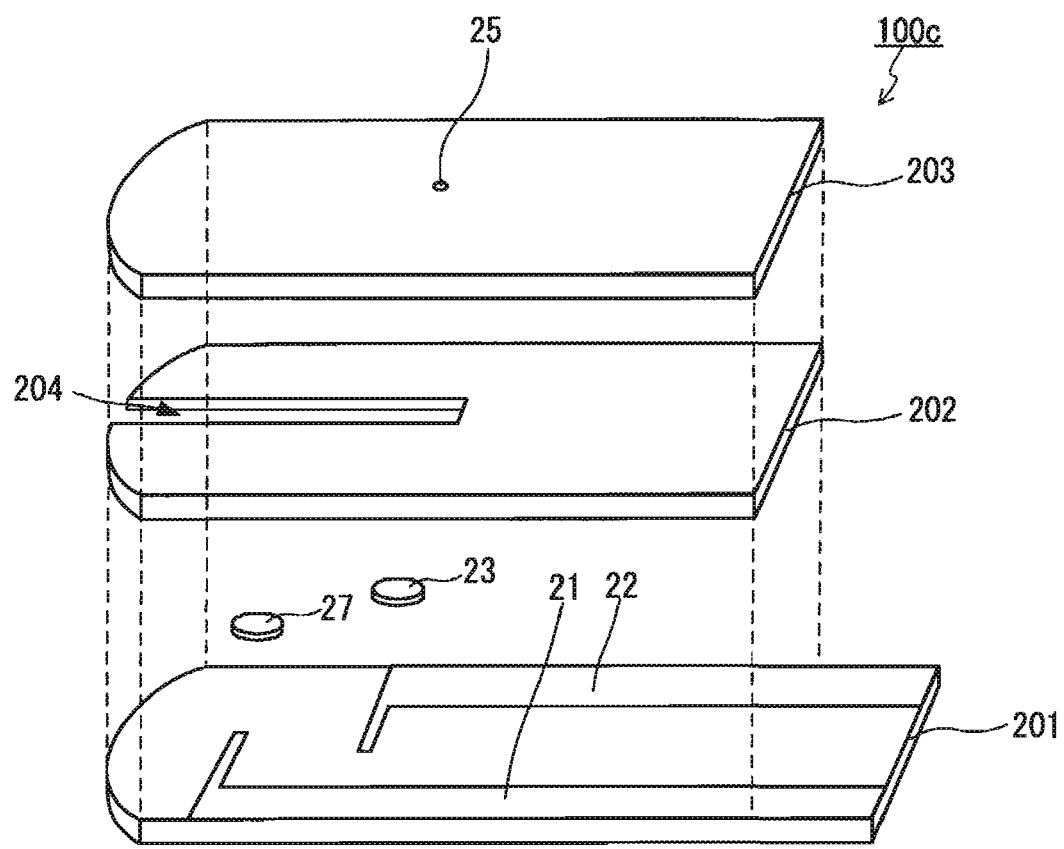
FIG. 3 is an exploded perspective view showing another example of a sensor chip for measuring a Hct value of the present invention.
Figure 4:
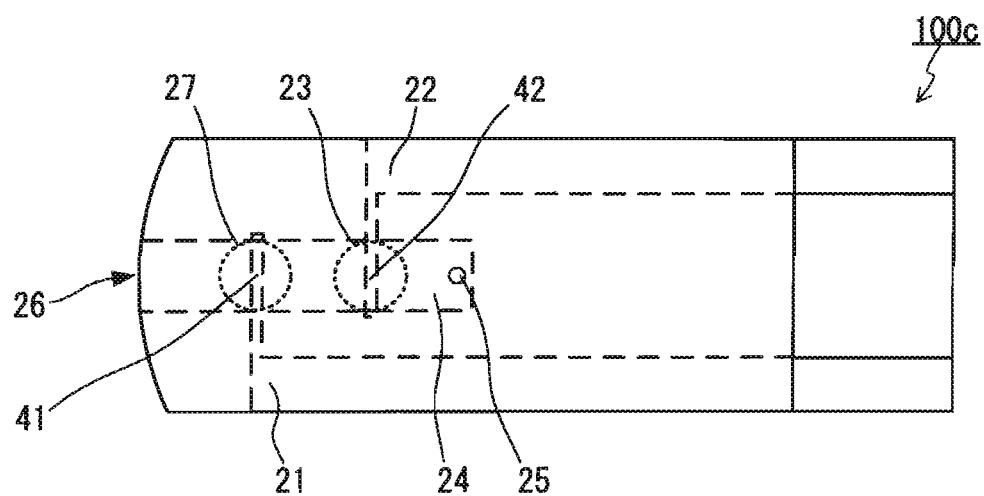
FIG. 4 is a plan view showing another example of a sensor chip for measuring a Hct value of the present invention.

FIG. 3 is an exploded perspective view of a sensor chip C for measuring a Hct value, and FIG. 4 is a plan view of the sensor chip shown in FIG. 3. As shown in the figures, a sensor chip C100c for measuring a Hct value includes a spacer 202 having a rectangular cutout portion 204, and insulating substrate 201, and a cover 203. The cover 203 is disposed on the insulating substrate 201 with the spacer 202 in between, leaving one end portion of the insulating substrate 201 uncovered (on the right in the figures). These members 201, 202, and 203 are integrated, for example, by bonding or heat fusion. The cutout portion 204 of the spacer 202 serves as a blood sample holder 24 after integration of the members. The blood sample holder 24 extends along the longer side of the chip 100c, and is in communication with outside at an end portion of the spacer 202 (on the left in the figures). In other words, the blood sample holder 24 is in communication with a blood sample inlet 26, which opens to outside of the chip 100c. The cover 203 includes an outlet 25, corresponding in position to a portion of the blood sample holder 24 at the opposite end of the end in communication with outside. A working electrode 21 and a counter electrode 22 are disposed on the insulating substrate 201 such that a portion (portion 41) of the working electrode 21 and a portion (portion 42) of the counter electrode 22 face the blood sample holder 24, and that the portion 41 is closer to a blood sample inlet 26 than the portion 42 is. The working electrode 21 and the counter electrode 22 each are connected to a lead (not shown). An end of each lead is exposed to outside of the chip 100c at the end portion of the insulating substrate 201 not covered with the spacer 202 and the cover 203, in order to apply a voltage across the working electrode and the counter electrode.

A first reagent 23 containing the oxidant of the redox substance and substantially not containing the reductant is disposed to cover the portion 42 of the counter electrode 22. A second reagent 27 containing the reductant of the redox substance and substantially not containing the oxidant is disposed to cover the portion 41 of the working electrode 21. Preferably, these reagents do not easily dissolve into the blood sample.

<Sensor Chip D for Measuring Hct Value>

Figure 5:
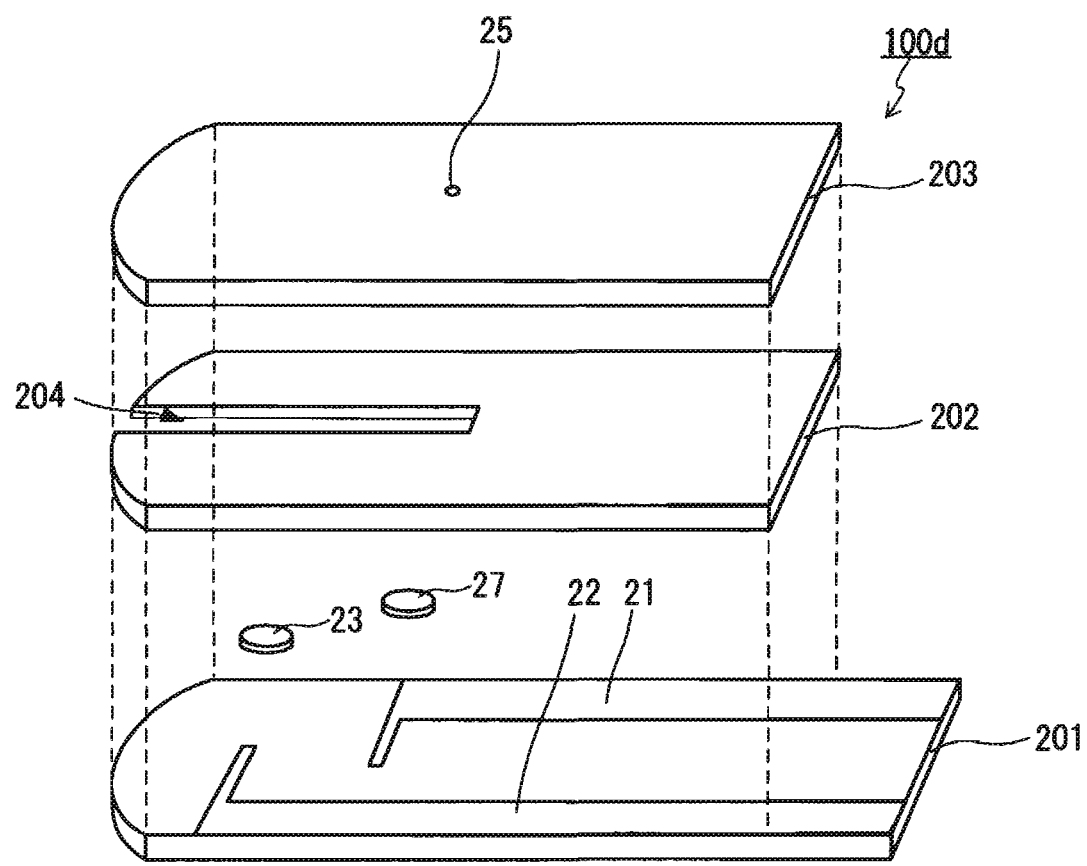
FIG. 5 is an exploded perspective view showing another example of a sensor chip for measuring a Hct value of the present invention.
Figure 6:
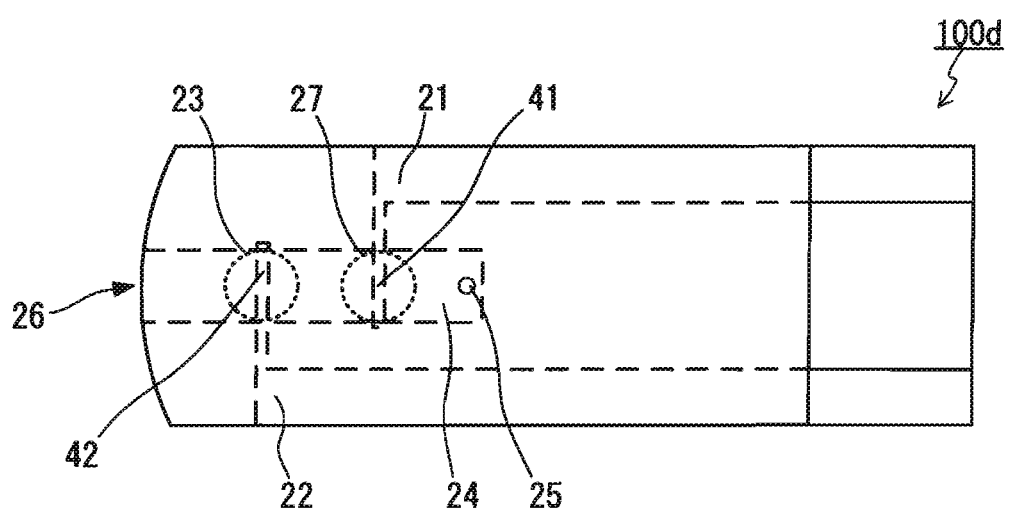
FIG. 6 is a plan view showing another example of a sensor chip for measuring a Hct value of the present invention.
Figure 7:
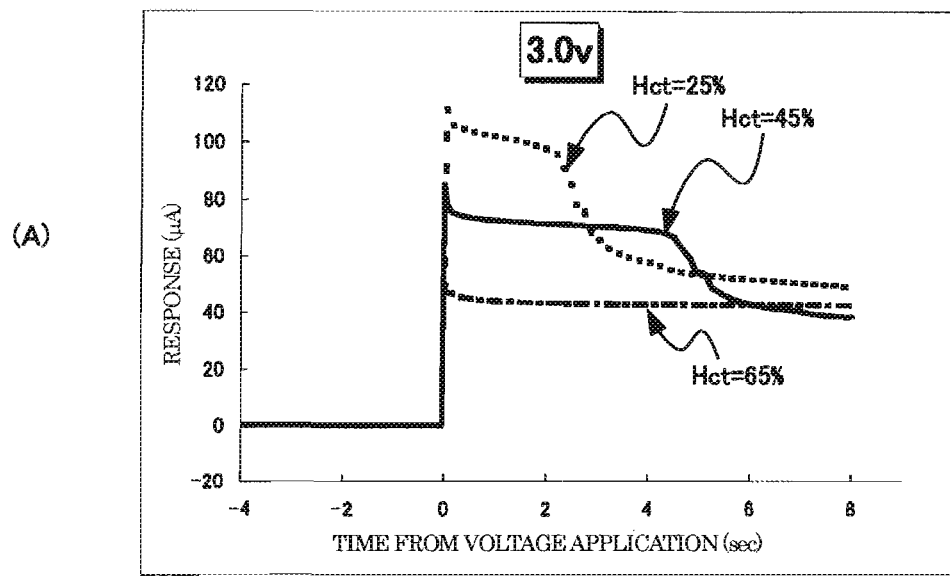
FIG. 7 is a graph representing an example of measurement results of Hct value by a sensor chip of Example 1.
Figure 7:
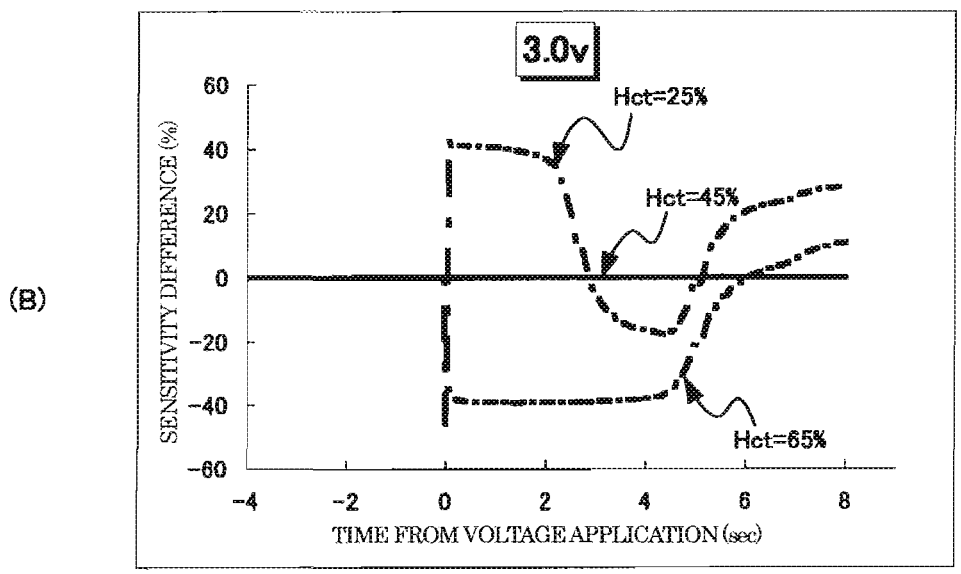
Figure 8:
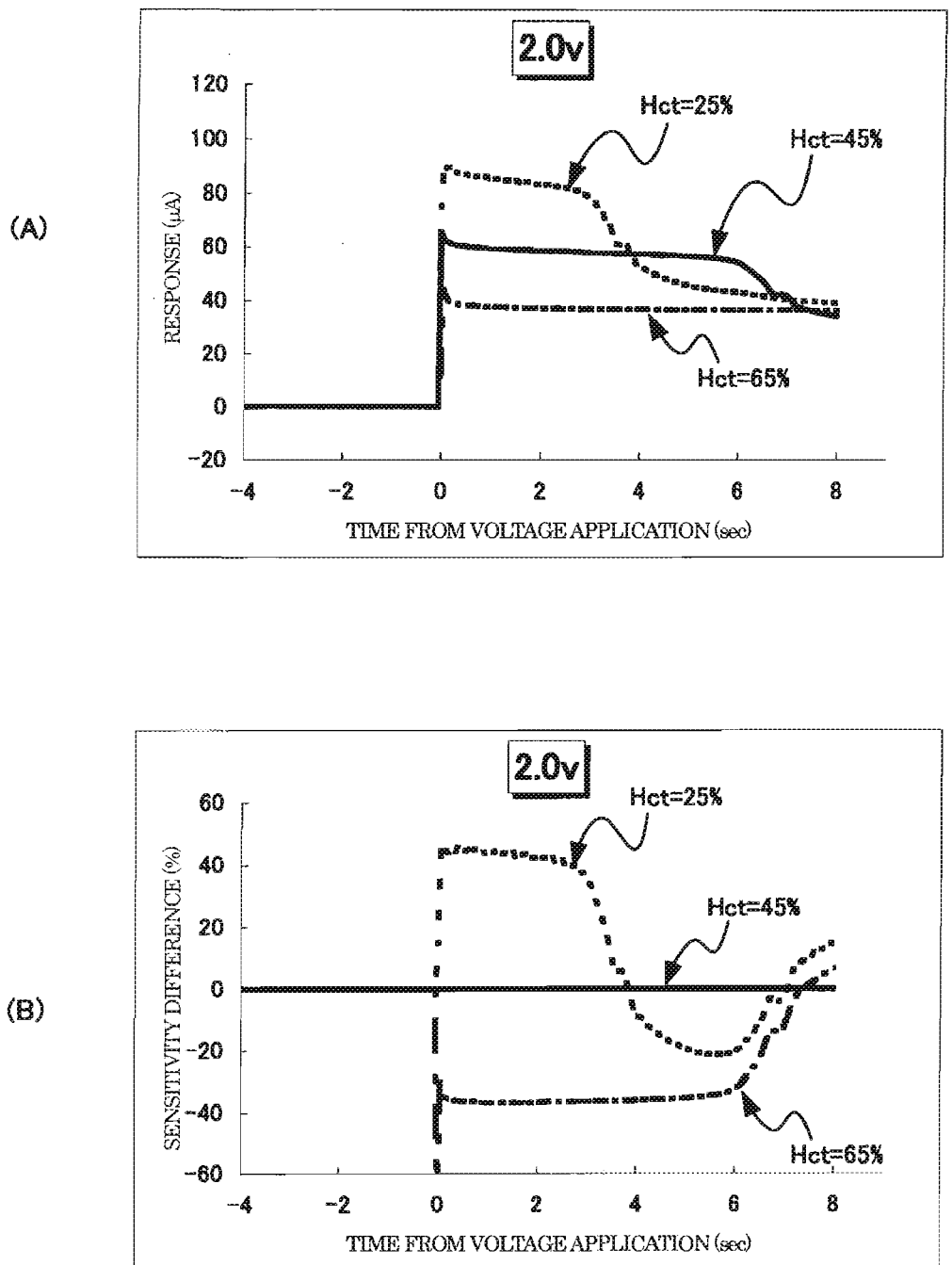
FIG. 8 is a graph representing another example of measurement results of Hct value by the sensor chip of Example 1.
Figure 9:
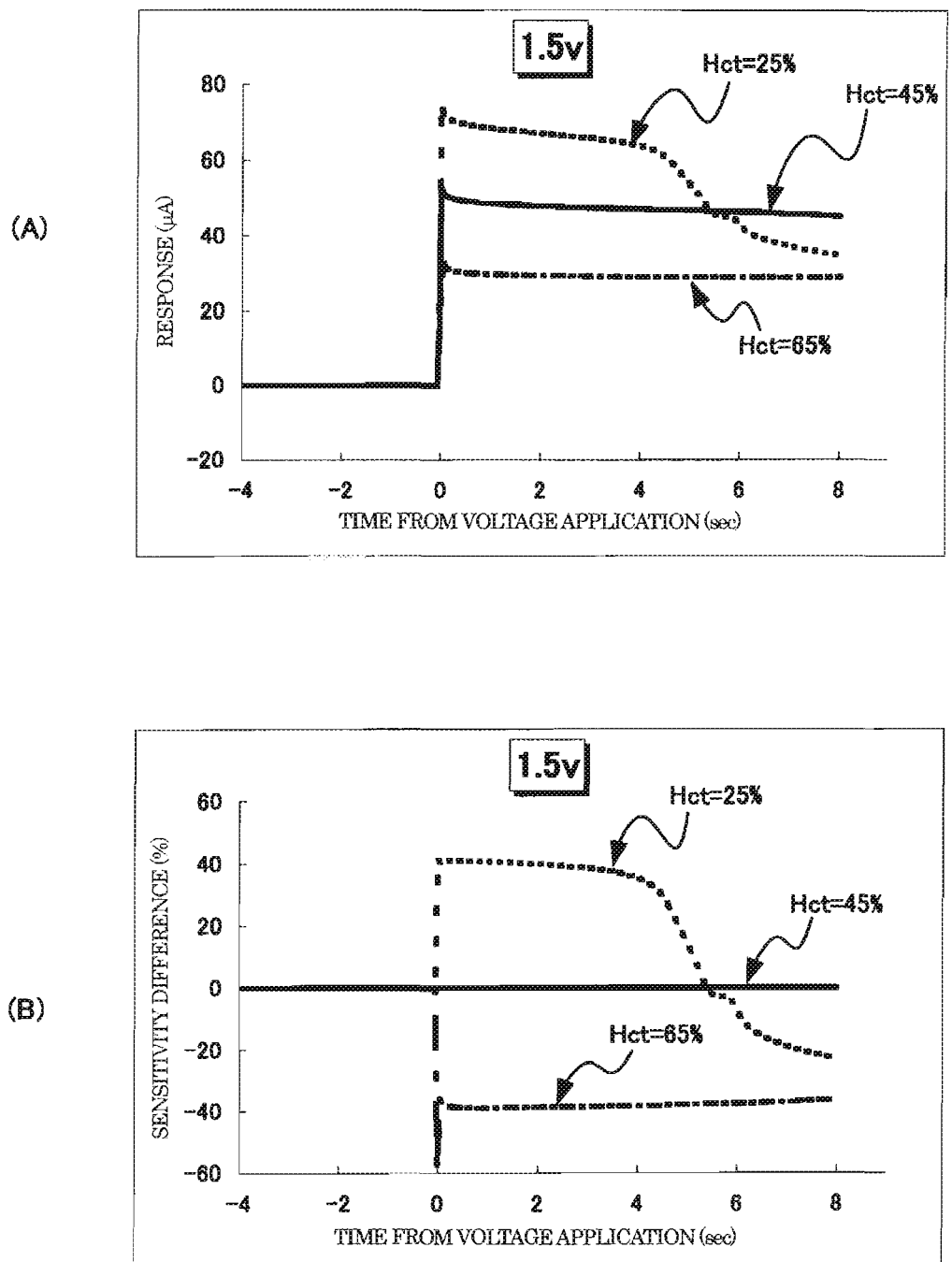
FIG. 9 is a graph representing another example of measurement results of Hct value by the sensor chip of Example 1.
Figure 10:
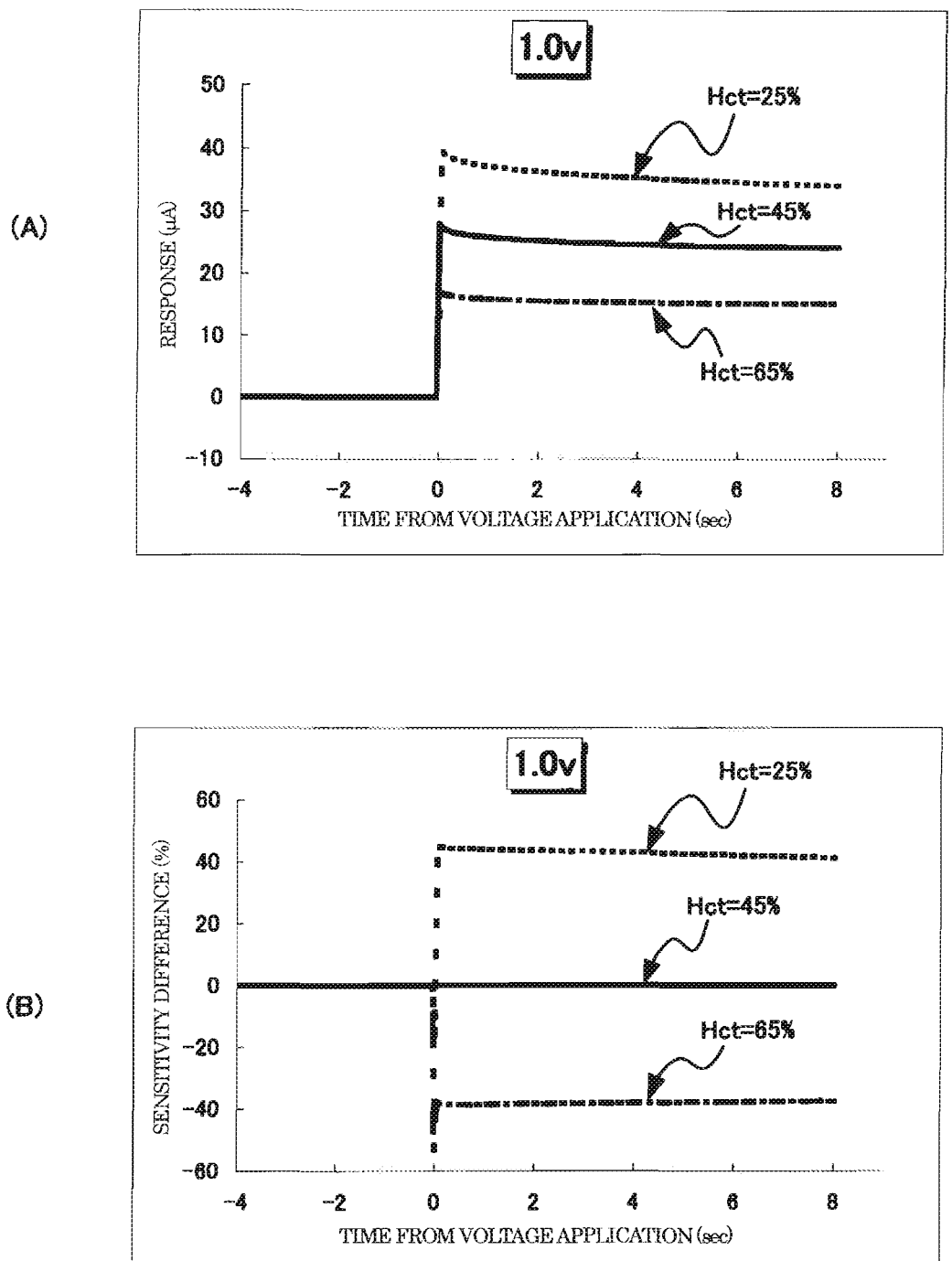
FIG. 10 is a graph representing another example of measurement results of Hct value by the sensor chip of Example 1.
Figure 11:
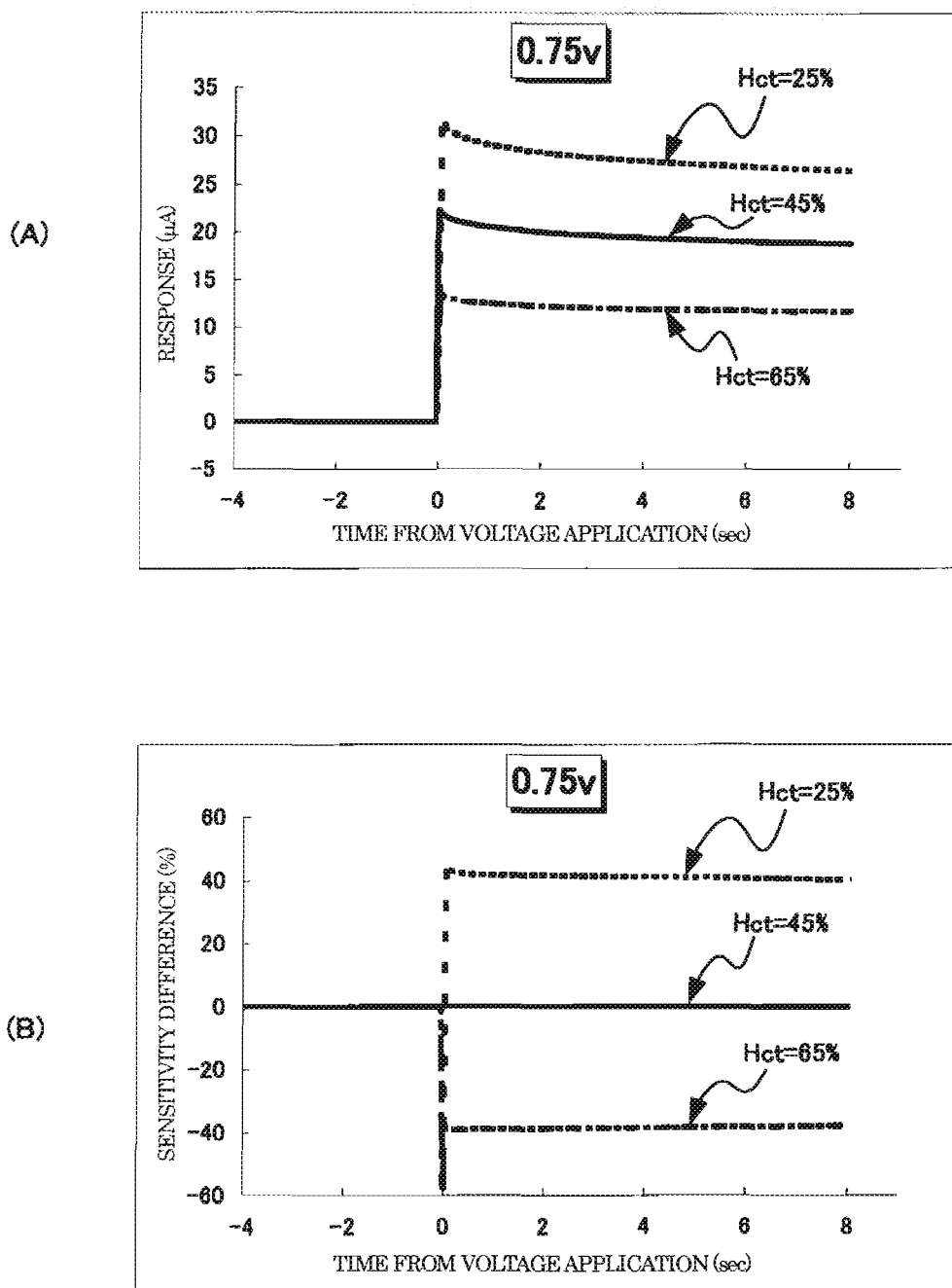
FIG. 11 is a graph representing another example of measurement results of Hct value by the sensor chip of Example 1.
Figure 12:
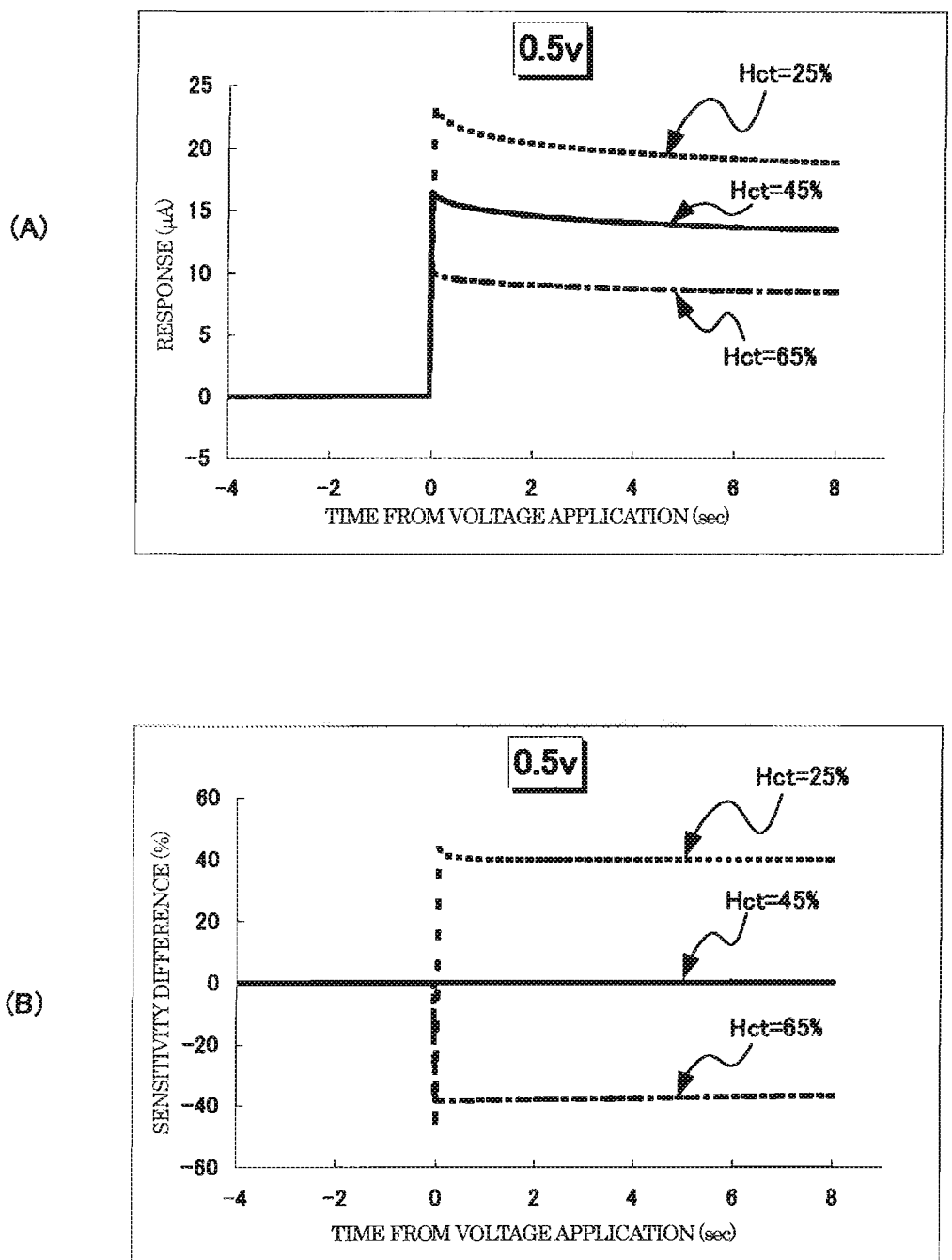
FIG. 12 is a graph representing another example of measurement results of Hct value by the sensor chip of Example 1.
Figure 13:
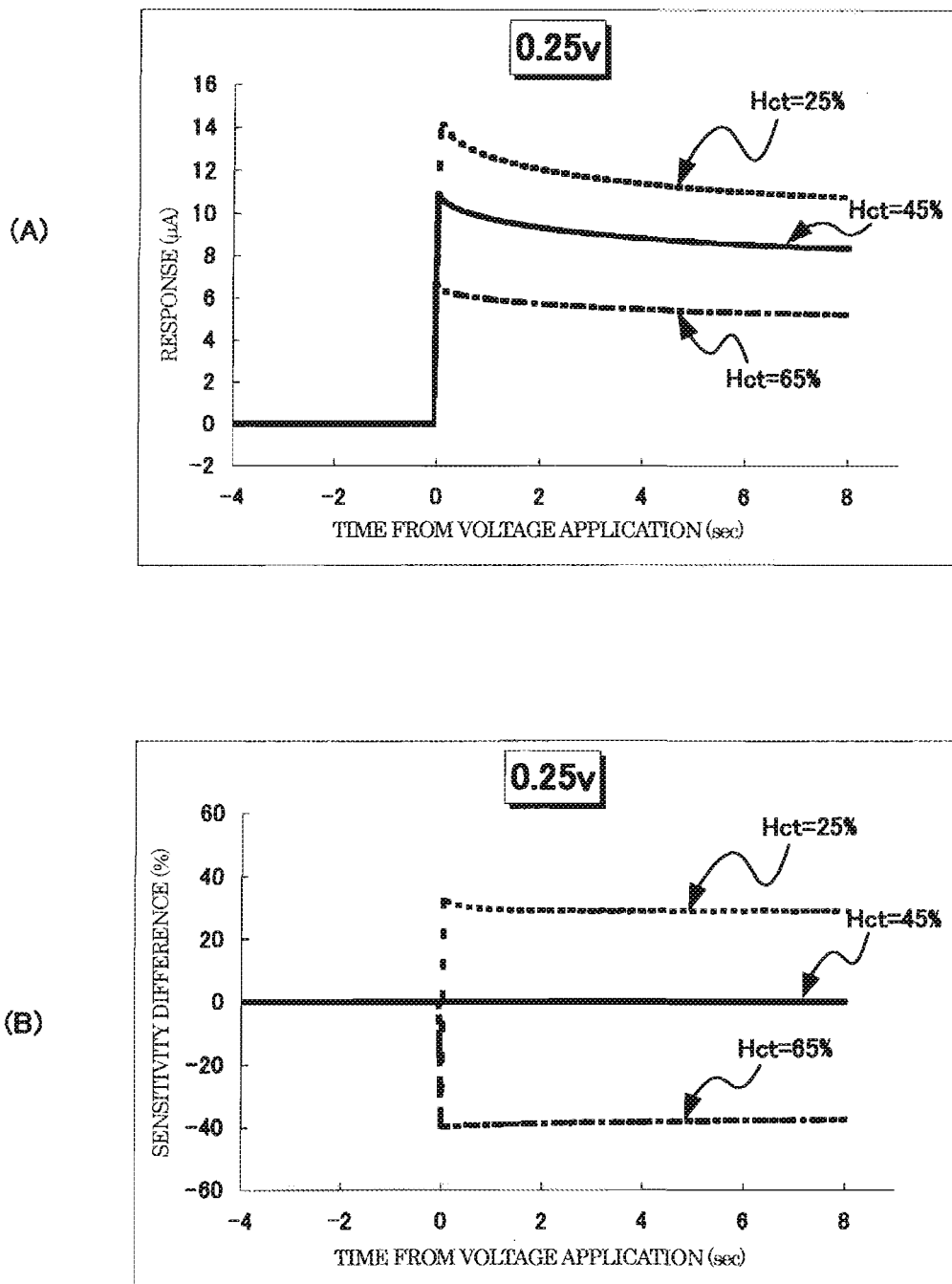
FIG. 13 is a graph representing another example of measurement results of Hct value by the sensor chip of Example 1.
Figure 14:
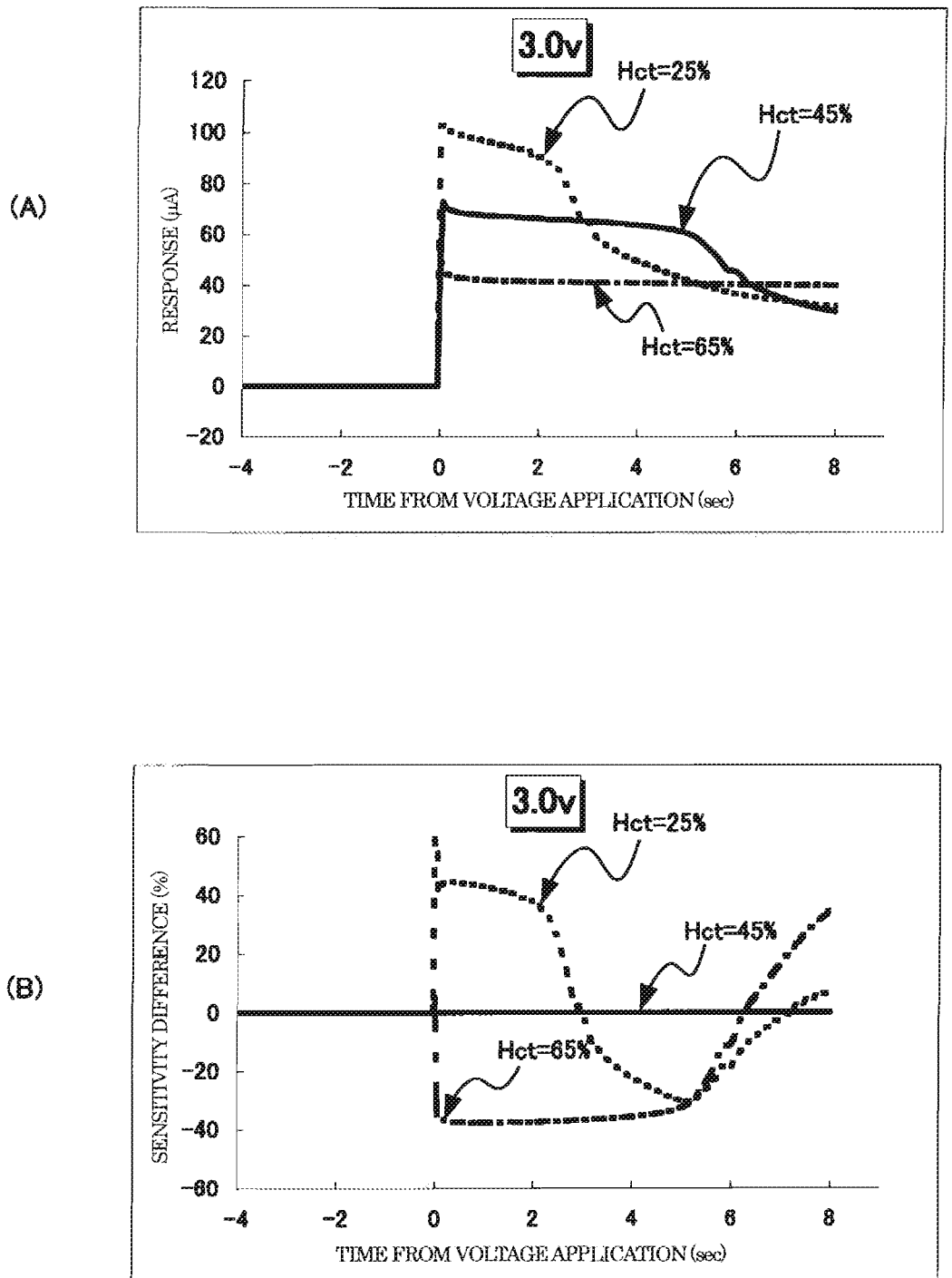
FIG. 14 is a graph representing an example of measurement results of Hct value by a sensor chip of Example 2.
Figure 15:
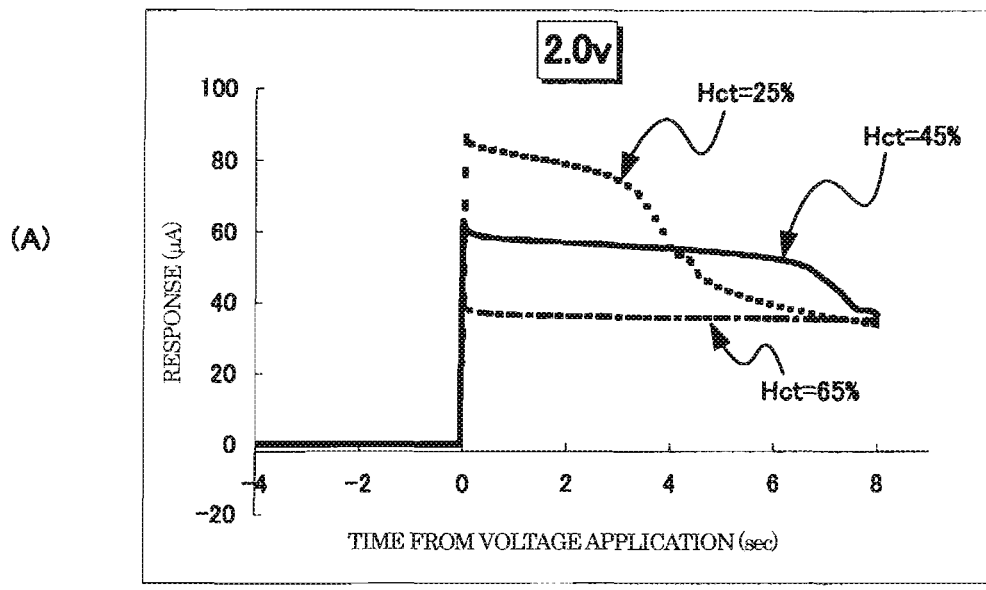
FIG. 15 is a graph representing another example of measurement results of Hct value by the sensor chip of Example 2.
Figure 15:
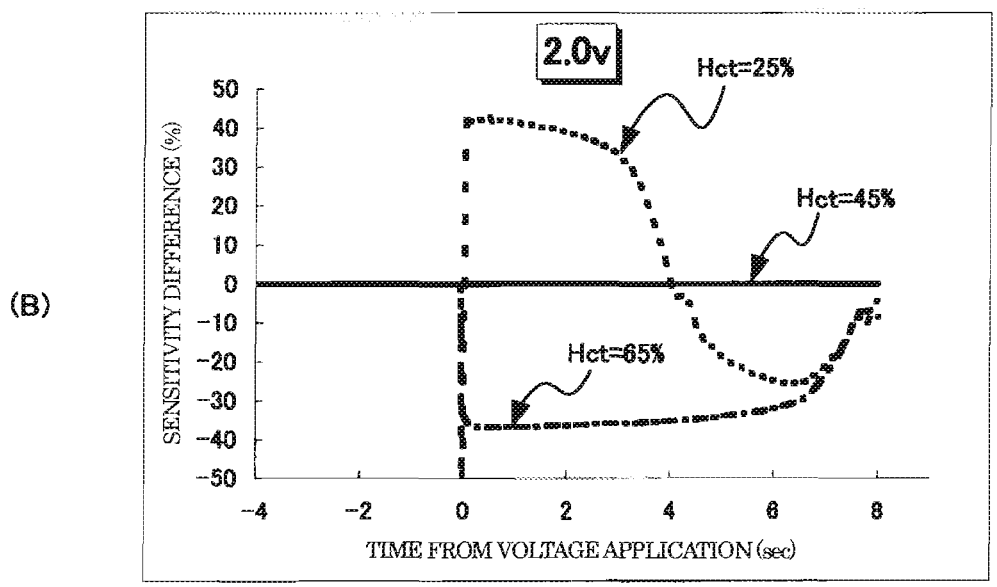
Figure 16:
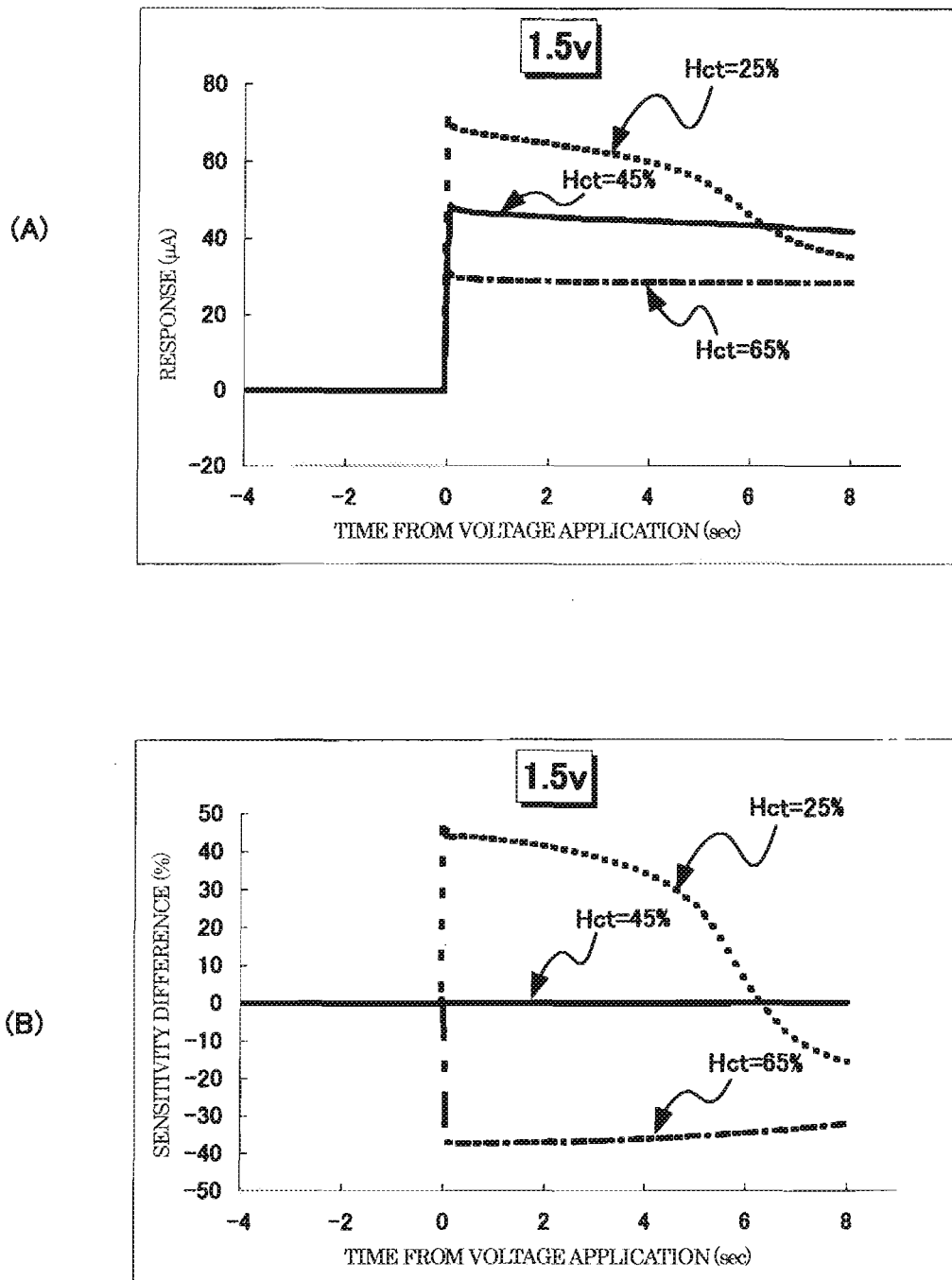
FIG. 16 is a graph representing another example of measurement results of Hct value by the sensor chip of Example 2.
Figure 17:
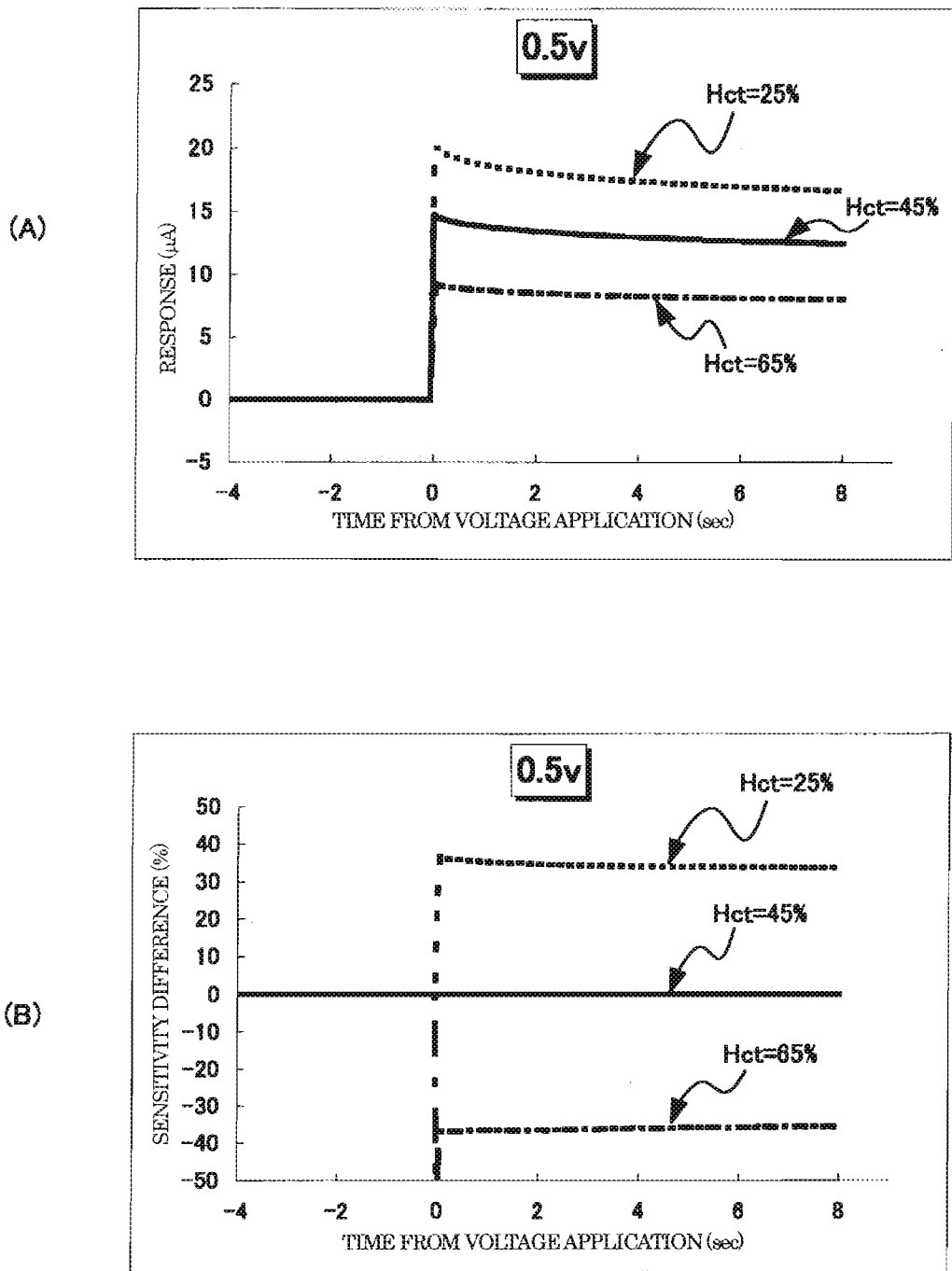
FIG. 17 is a graph representing another example of measurement results of Hct value by the sensor chip of Example 2.
Figure 18:
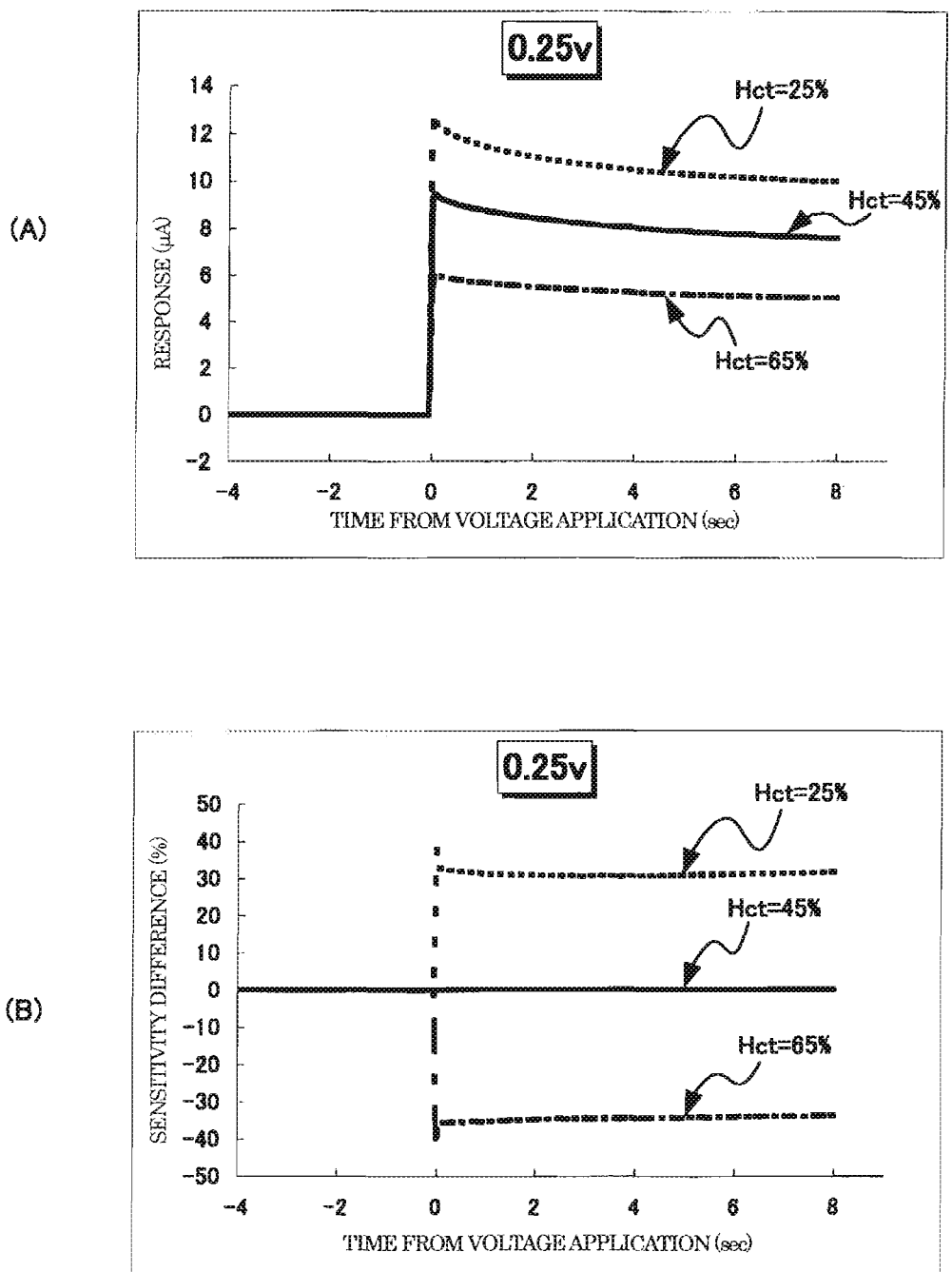
FIG. 18 is a graph representing another example of measurement results of Hct value by the sensor chip of Example 2.
Figure 19:
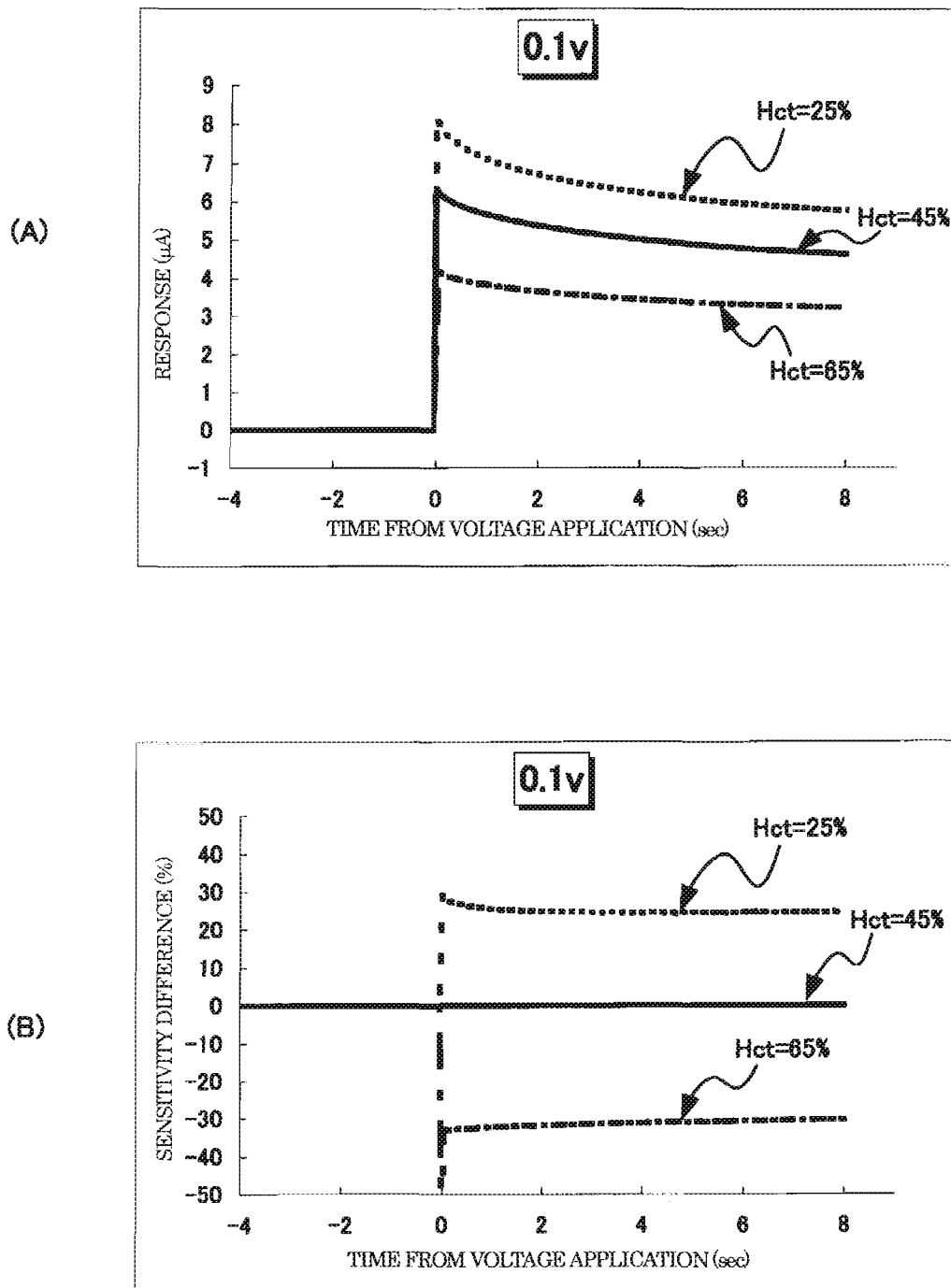
FIG. 19 is a graph representing another example of measurement results of Hct value by the sensor chip of Example 2.

FIG. 5 is an exploded perspective view of a sensor chip D for measuring a Hct value, and FIG. 6 is a plan view of the sensor chip shown in FIG. 5. As shown in the figures, a sensor chip D100d for measuring a Hct value has the same configuration as the sensor chip C for measuring a Hct value except that the counter electrode 22 and the working electrode 21 are disposed on the insulating substrate 201 such that the portion 42 of the counter electrode 22 is closer to the blood sample inlet 26 than the portion 41 of the working electrode 21 is, and that the first reagent 23 and the second reagent 27 are disposed to cover the portion 42 of the counter electrode 22 and the portion 41 of the working electrode 21, respectively. Preferably, these reagents do not easily dissolve into the blood sample.

The measurement of the Hct value of the blood sample by the sensor chip for measuring a Hct value can be performed using, for example, a sensor unit for measuring a Hct value, which is an example of a sensor unit of the present invention.

The sensor unit for measuring a Hct value includes a sensor chip for measuring a Hct value, and a sensor main body detachably provided with the sensor chip. The sensor main body includes a voltage applying circuit capable of applying a predetermined voltage across the working electrode and the counter electrode of the sensor chip with the sensor chip attached to the sensor main body.

The voltage applying circuit applies a voltage of 3.0 V or less across the working electrode and the counter electrode, when the working electrode of the anode and the counter electrode is the cathode. The applied voltage may be, for example, 1.0 V or less, 0.75 V or less, 0.5 V or less, 0.25 V or less, 0.15 V or less, or 0.1 V or less. The lower limit of the voltage is not particularly limited as long as the reductant is oxidized at the working electrode and the oxidant is reduced at the counter electrode. However, the voltage is desirably 0 V or greater, when the working electrode is the anode and the counter electrode is the cathode.

Figure 26:
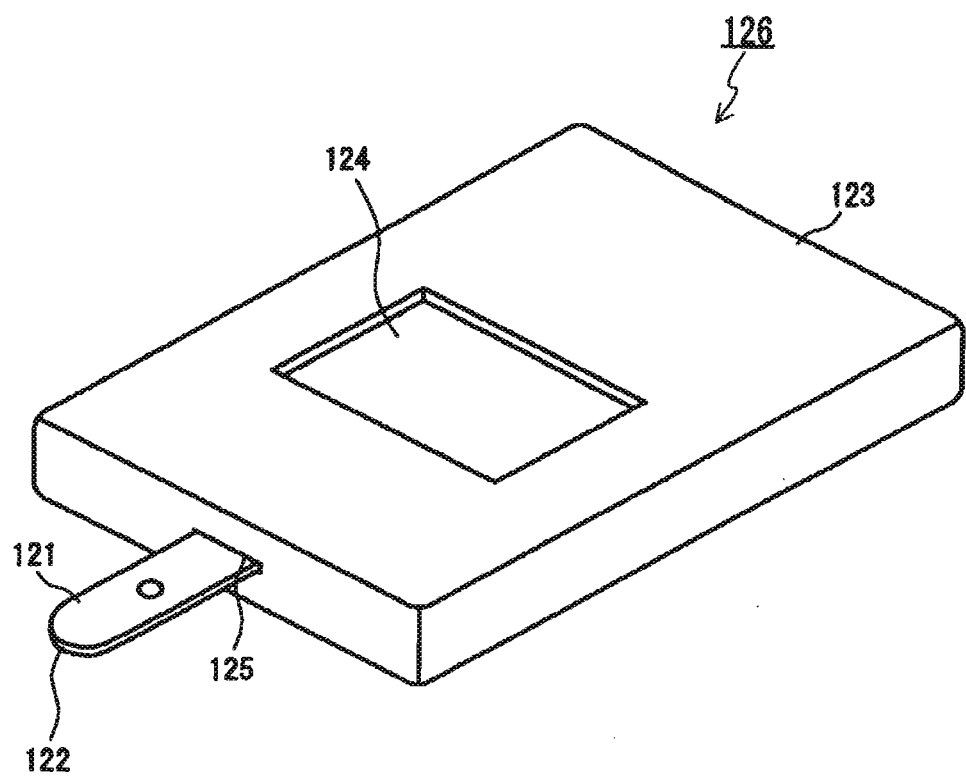
FIG. 26 is a perspective view showing an example of a sensor unit for measuring a Hct value of the present invention.

FIG. 26 is a diagram showing an example of the sensor unit for measuring a Hct value. A sensor unit 126 for measuring a Hct value includes a flat hexahedral sensor main body 123, and a sensor chip 121 for measuring a Hct value. Through one side wall surface of the sensor main body 123, an attachment opening 125 is provided in the shape of a rectangular aperture. The sensor chip 121 is attached to the sensor main body 123 by being detachably coupled to the attachment opening 125. A display section 124 for displaying a measurement result of Hct value is provided substantially at the center of one principal surface of the sensor main body 123.

Figure 27:
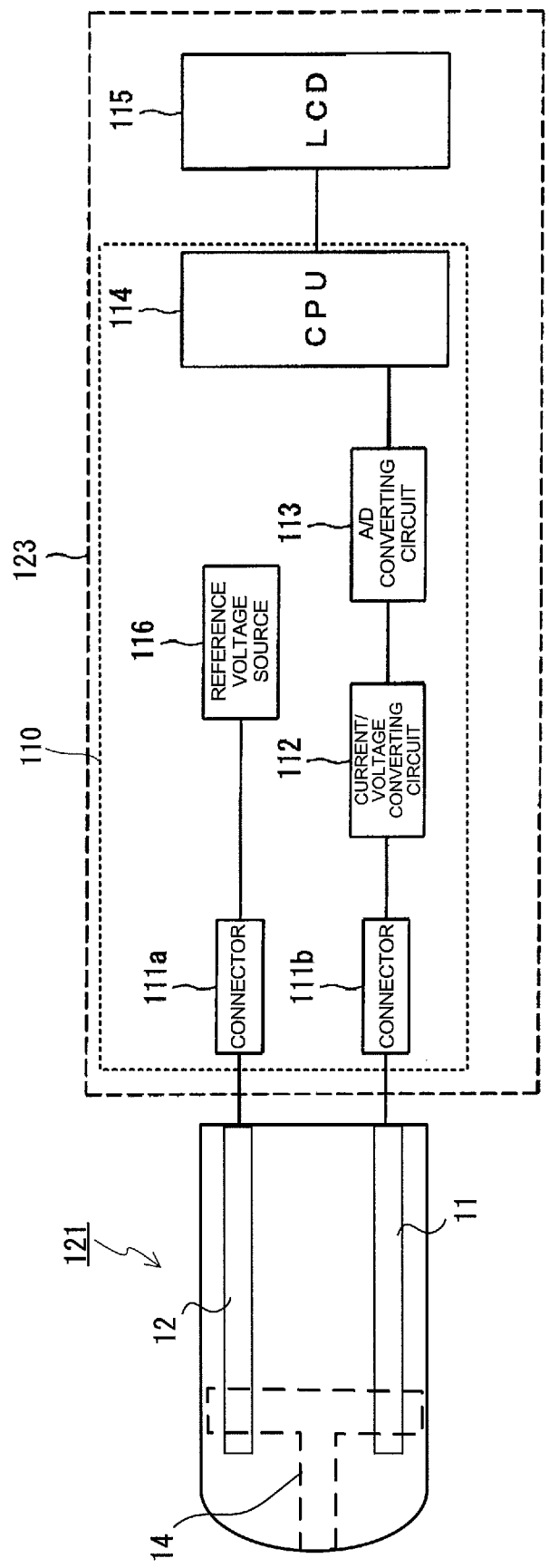
FIG. 27 is a diagram showing an example of a circuit structure of a sensor unit for measuring a Hct value of the present invention.

FIG. 27 is a diagram showing an exemplary circuit structure for measuring a Hct value in the sensor unit 126 for measuring a Hct value. The sensor main body 123 includes a voltage applying circuit 110 for applying a predetermined voltage across the working electrode 11 and the counter electrode 12 of the sensor chip 121, and a liquid crystal display (LCD) 115 as the display section 124. The voltage applying circuit 110 includes two connectors 111a and 111b, a current/voltage converting circuit 112, an A/D converting circuit 113, a central processing unit (CPU) 114, and a reference voltage source 116. These elements 111a, 111b, 112, 113, 114, 115, and 116 are connected electrically to one another, as indicated by the solid lines in FIG. 27.

The measurement of the Hct value of the blood sample using the sensor unit 126 proceeds as follows, for example. First, a blood sample is introduced into the blood sample holder 14 of the sensor chip 121 through a blood sample inlet 122 of the sensor chip 121. Then, under an instruction from the CPU 114, a predetermined Hct value measuring voltage is applied across the working electrode 11 and the counter electrode 12 by the current/voltage converting circuit 112 and the reference voltage source 116. The Hct value measuring voltage is applied for an adjusted time period in the foregoing range, for example, 0.001 to 60 seconds, preferably 0.01 to 10 seconds, more preferably 0.01 to 5 seconds, and even more preferably 0.01 to 3 seconds. The value of the current flown between the working electrode 11 and the counter electrode 12 by the application of the Hct value measuring voltage is converted to a voltage value by the current/voltage converting circuit 112. This voltage value is then converted to a digital value by the A/D converting circuit 113 before it is sent to the CPU 114. The CPU 114 calculates a Hct value based on the digital value. The Hct value is calculated, for example, by referring to a standard curve or a standard table, relating the Hct value of a blood sample to the amount of current after a predetermined time period from the application of the Hct value measuring voltage. The result of calculation is visually displayed on the LCD 115.

With a method for measuring a Hct value of a blood sample of the present invention, the analyte concentration in the blood sample can be measured with improved accuracy. The analyte concentration in the blood sample is determined based on data C, which is obtained by correcting preliminary measurement data (data B) of the analyte in the blood sample using data A, which corresponds to the Hct value of the blood sample.

The data A corresponding to the Hct value of the blood sample is obtained by a method for measuring a Hct value of a blood sample of the present invention. The data A may be a value that results from the conversion of current A into a Hct value, wherein the current A is a current flowing through the working and counter electrodes for Hct value measurement (a working and a counter electrode for correction), reflecting the Hct value of the blood sample. Alternatively, the data A may be a value obtained by the conversion of the current A into some other parameter different from the Hct value. Further, the data A may be the current A itself. The conversion of the current A into a Hct value is performed, for example, by referring to a standard curve or a standard table, relating current A to Hct value after a predetermined time period from the application of the Hct value measuring voltage.

Current B is detected to obtain data B. The current B is a current flowing between a working electrode (working electrode for preliminary measurement) and a counter electrode (counter electrode for preliminary measurement), as a result of applying a voltage (preliminary measuring voltage) across these electrodes in contact with a blood sample after a certain time period of reaction between the analyte in the blood sample and a redox enzyme that uses the analyte as a substrate. The data B may be, for example, a value that results from the conversion of the current B into a preliminary measurement concentration of the analyte. Alternatively, the data B may be, for example, a value obtained by the conversion of the current B into some other parameter different from the preliminary measurement concentration. Further, the data B may be the current B itself, for example. The conversion of the current B into a preliminary measurement concentration is performed, for example, by referring to a standard curve or a standard table, relating current B to preliminary measurement concentration after a predetermined time period from the application of the preliminary measuring voltage.

The current B is detected using a redox substance, for example, a reversible electroactive compound as represented by ferricyanide, which mediates the movement of electrons between the enzyme reaction and the electrode reaction. The content of the redox substance in the blood sample brought into contact with the working electrode for preliminary measurement and the counter electrode for preliminary measurement may be 0.1 to 1000 mM, for example. In the detection of current B, the redox enzyme and the redox substance may be in contact with the counter electrode for preliminary measurement and the working electrode for preliminary measurement by being contained in the blood sample brought into contact with these electrodes, for example. Alternatively, the redox enzyme and the redox substance directly may be disposed on these electrodes, for example. Further, the redox enzyme and the redox substance may be embedded in the surfaces of these electrodes, for example. That is, in the detection of current B, the redox enzyme and the redox substance may be in contact with the electrodes by being dissolved in the blood sample, or by being provided as a solid.

The analyte in the blood sample may be a substance other than blood cells. Some of the examples include glucose, albumin, lactic acid, bilirubin, and cholesterol. The redox enzyme is selected according to the type of substrate, i.e., the analyte being analyzed. Examples of the redox enzyme include glucose oxidase, glucose dehydrogenase, lactate oxidase, lactate dehydrogenase, bilirubin oxidase, and cholesterol oxidase. The amount of redox enzyme that reacts with the analyte may be set such that the content of the redox enzyme in the blood sample is, for example, 0.01 to 100 units (U), 0.05 to 10 U, or in some cases, 0.1 to 5 U.

The reaction time of the analyte and the redox enzyme may be, for example, 0 to 60 seconds, 0.5 to 30 seconds, or in some cases, 1 to 10 seconds. The preliminary measuring voltage may be, for example, 0.05 to 1 V, 0.1 to 0.8 V, or in some cases, 0.2 to 0.5 V, when the working electrode for preliminary measurement is the anode and the counter electrode for preliminary measurement is the cathode. The preliminary measuring voltage may be applied for, for example, 0.01 to 30 seconds, 0.1 to 10 seconds, or in some cases, 1 to 5 seconds.

The counter electrode for preliminary measurement or the working electrode for preliminary measurement may be provided separately from the counter electrode for correction or the working electrode for correction. Alternatively, part of or all of the counter electrode for correction or the working electrode for correction may be used as the counter electrode for preliminary measurement or the working electrode for preliminary measurement. For example, the working electrode for preliminary measurement also may be used as the counter electrode for correction.

The counter electrode for preliminary measurement and the working electrode for preliminary measurement can be configured in the same manner as the counter electrode for correction. The shape, size, and layout pattern of the counter electrode for preliminary measurement and the working electrode for preliminary measurement are not particularly limited.

The order of detecting the current A and current B is not particularly limited. For example, when the working electrode for preliminary measurement and the counter electrode for correction are realized by a single electrode as mentioned above, it is preferable that the current A be detected after detecting the current B, considering the possible shortage of the redox substance of the form brought into contact with the electrode in the detection of each current. This needs to be prevented because the redox reaction on the electrode becomes a rate-limiting step in this case.

As described, the analyte concentration in the blood sample is determined based on data C, which is obtained by correcting data B with data A. The resulting value of data C corresponds to data B. The data C may be, for example, the analyte concentration itself in the blood sample, or a corrected current value. When the value of data C is not the analyte concentration itself, the analyte concentration in the blood sample is determined by referring to a standard curve or a standard table, relating the value of data C to the analyte concentration in the blood sample.

The analyte concentration in the blood sample can be measured using a sensor chip for measuring an analyte concentration, which is another example of a sensor chip of the present invention.

The sensor chip for measuring an analyte concentration includes a Hct value analyzer, analogous to that in the sensor chip for measuring a Hct value.

The sensor chip for measuring an analyte concentration includes an analyzer for preliminary measurement, used for electrochemical detection of the current B. The analyzer for preliminary measurement may be provided separately from the Hct value analyzer, or part of or all of the Hct value analyzer may be used as the analyzer for preliminary measurement. For example, the electrode system (electrode system A), the blood sample holder (blood sample holder A), and the blood sample inlet (blood sample inlet A) of the Hct value analyzer may be used to realize an electrode system (electrode system B) including the working electrode for preliminary measurement and the counter electrode for preliminary measurement, a blood sample holder (blood sample holder B) for holding the blood sample in contact with the working electrode for preliminary measurement and the counter electrode for preliminary measurement, and a blood sample inlet (blood sample inlet B) in communication with the blood sample holder B, respectively.

When the analyzer for preliminary measurement is separately provided from the Hct value analyzer, the blood sample inlet B of the analyzer for preliminary measurement may be provided more toward the downstream side compared to the Hct value analyzer, with respect to the flow of the blood sample introduced into the sensor chip, so that, in the detection of current A, the oxidant of the redox substance will not be in contact with the working electrode for correction as a result of the inflow of the blood sample. When part of or all of the Hct value analyzer is used as the analyzer for preliminary measurement, the layout pattern of the reagent containing the oxidant, the shape of the blood sample holder, and the layout pattern of each electrode system may be set in the manner described later. Note that, when at least part of the electrode system A is used to realize the electrode system B, the working electrode for preliminary measurement and the counter electrode for correction may be realized by a single electrode, as described above.

The working electrode for preliminary measurement and the counter electrode for preliminary measurement at least partially face the blood sample holder B, so as to be in contact with the blood sample introduced into the blood sample holder B.

Desirably, the shape and volume of the blood sample holder B are set such that the blood sample can be introduced therein by capillary action.

The analyzer for preliminary measurement may include the redox enzyme and the redox substance associated with the enzymatic cycling reaction for the preliminary measurement of the analyte concentration.

The redox enzyme may contain an enzyme stabilizer as represented by, for example, a sugar alcohol such as maltitol, sorbitol, and xylitol. The amount of redox enzyme in the analyzer for preliminary measurement may be set such that the content of the redox enzyme in the blood sample is, for example, 0.01 to 100 units (U), 0.05 to 10 U, or in some cases, 0.1 to 5 U.

FIGS. 30 through 35, and FIGS. 37 and 38 are diagrams depicting specific examples of the layout pattern of the reagent containing the oxidant, the shape of the blood sample holder, and the layout pattern of the electrode system in the sensor chip for measuring an analyte concentration. In all of these examples, the analyzer for preliminary measurement and the Hct value analyzer share some of the same components. Specifically, the working electrode for preliminary measurement and the counter electrode for correction are realized by a single electrode, and the blood sample holder A and the blood sample inlet A also serve as the blood sample holder B and the blood sample inlet B, respectively.

<Sensor Chip A for Measuring Analyte Concentration>

Figure 30:
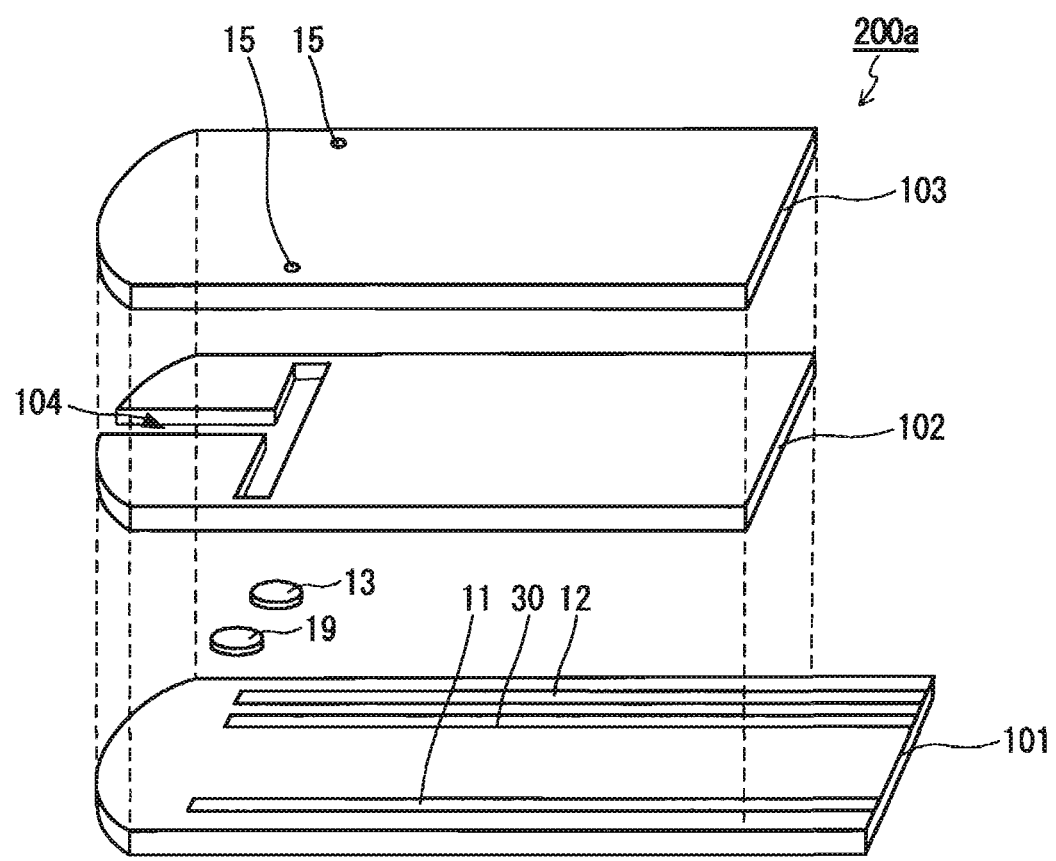
FIG. 30 is an exploded perspective view showing an example of a sensor chip for measuring an analyte concentration of the present invention.
Figure 31:
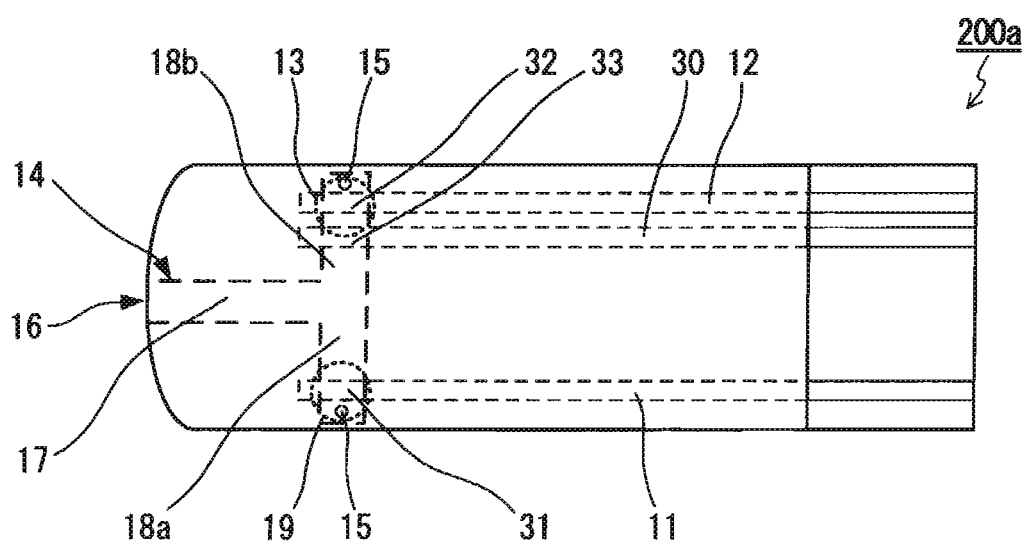
FIG. 31 is a plan view showing an example of a sensor chip for measuring an analyte concentration of the present invention.

FIG. 30 is an exploded perspective view of a sensor chip A for measuring an analyte concentration, and FIG. 31 is a plan view of the sensor chip shown in FIG. 30. As shown in the figures, a sensor chip A200a for measuring an analyte concentration has the same configuration as the sensor chip A100a for measuring a Hct value except that a counter electrode 30 for preliminary measurement is disposed on the insulating substrate 101 such that a portion (portion 33) of the counter electrode 30 for preliminary measurement faces the branch portion 18b and is closer to the inlet portion 17 than the portion 32 is. The counter electrode 12 also serves as the working electrode for preliminary measurement. The counter electrode 30 for preliminary measurement is connected to a lead (not shown). An end of the lead is exposed to the outside of the chip 200a at the end portion of the insulating substrate 101 not covered with the spacer 102 and the cover 103.

Another electrode may be disposed on the insulating substrate. For example, a blood detecting electrode for detecting an inflow of a sufficient measurement amount of blood sample into the blood sample holder may be disposed on the insulating substrate such that a portion of the blood detecting electrode faces the blood sample holder and is farther from the blood sample inlet than the portion 33 is.

<Sensor Chip B for Measuring Analyte Concentration>

Figure 37:
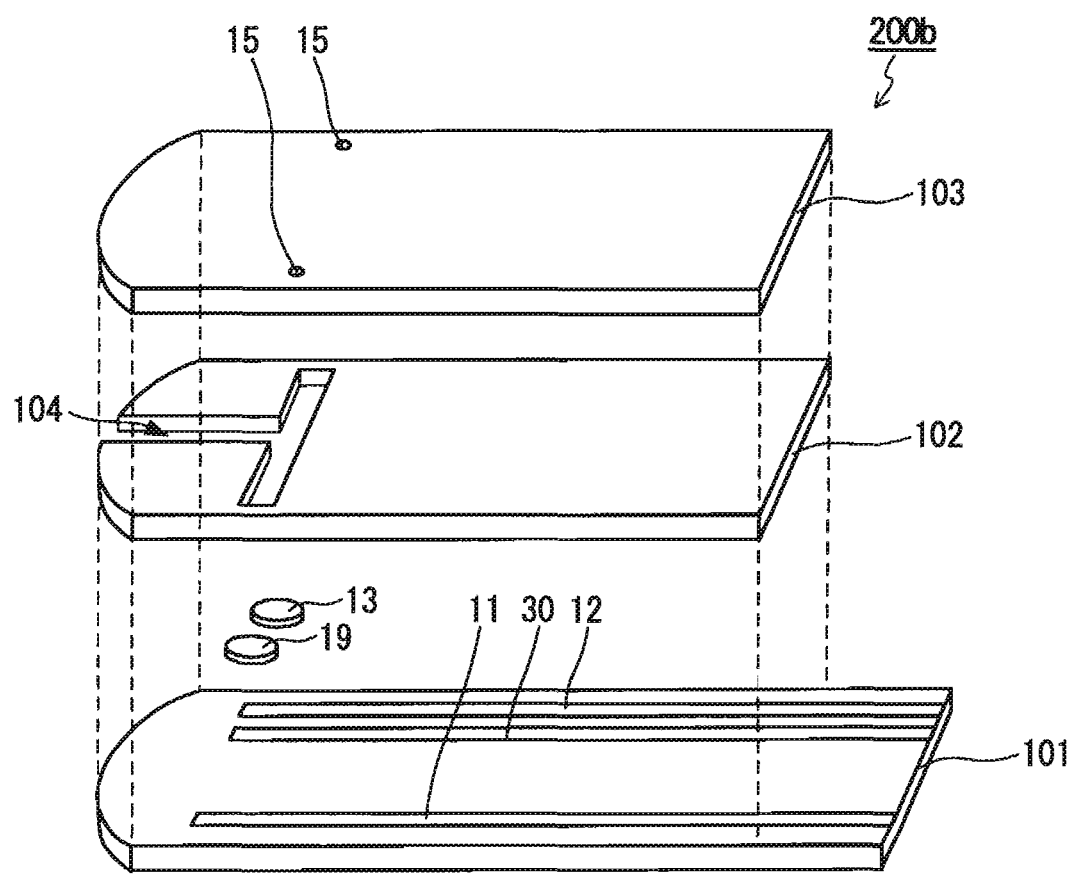
FIG. 37 is an exploded perspective view showing another example of a sensor chip for measuring an analyte concentration of the present invention.
Figure 38:
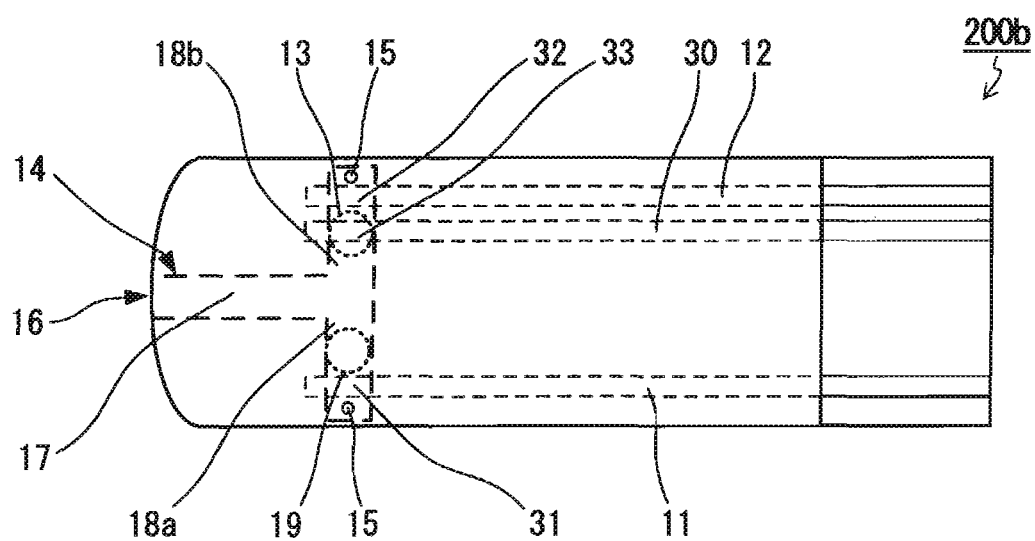
FIG. 38 is a plan view showing another example of a sensor chip for measuring an analyte concentration of the present invention.

FIG. 37 is an exploded perspective view of a sensor chip B for measuring an analyte concentration, and FIG. 38 is a plan view of the sensor chip shown in FIG. 37. As shown in the figures, a sensor chip B200b for measuring an analyte concentration has the same configuration as the sensor chip A for measuring an analyte concentration except that, in the branch portion 18a, the second reagent 19 is separated from the portion 31 of the working electrode 11 and is closer to the inlet portion 17 than the portion 31 is, and that, in the branch portion 18b, the first reagent 13 is separated from the portion 32 of the counter electrode 12 and is closer to the inlet portion 17 than the portion 32 is.

<Sensor Chip C for Measuring an Analyte Concentration>

Figure 32:
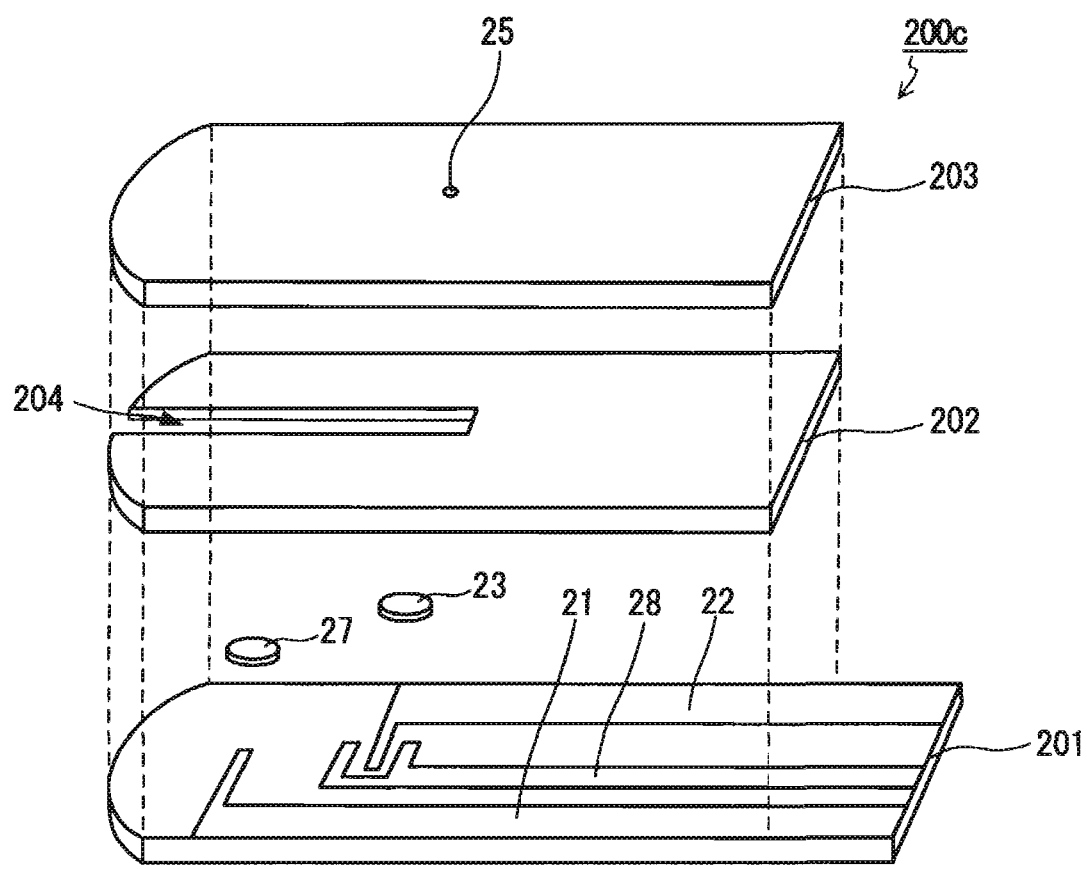
FIG. 32 is an exploded perspective view showing another example of a sensor chip for measuring an analyte concentration of the present invention.
Figure 33:
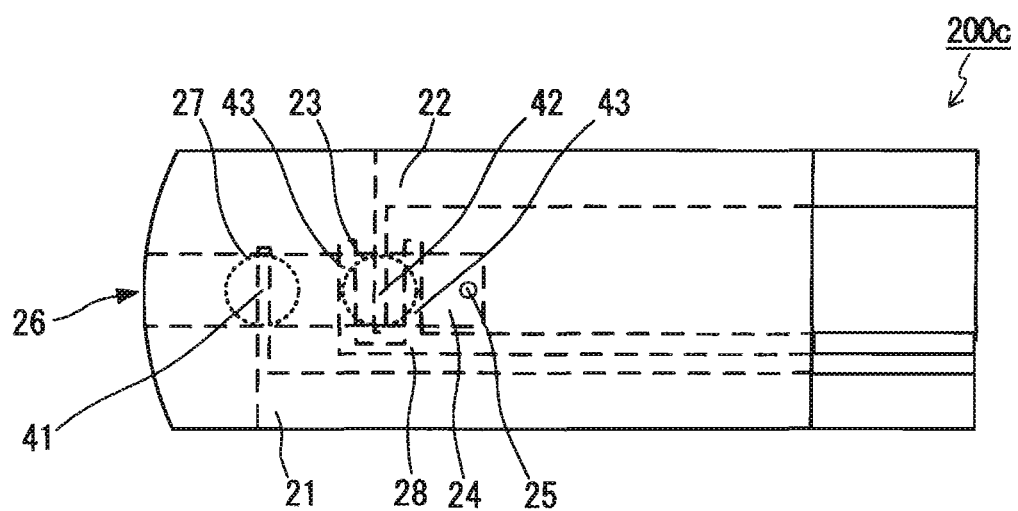
FIG. 33 is a plan view showing another example of a sensor chip for measuring an analyte concentration of the present invention.

FIG. 32 is an exploded perspective view of a sensor chip C for measuring an analyte concentration, and FIG. 33 is a plan view of the sensor chip shown in FIG. 32. As shown in the figures, a sensor chip C200c for measuring an analyte concentration has the same configuration as the sensor chip C100c for measuring a Hct value except that a counter electrode 28 for preliminary measurement, having a branched U-shaped portion (portion 43) facing the blood sample holder 24 and extending on the both sides of the portion 42 is disposed on the insulating substrate 201. The counter electrode 22 also serves as the working electrode for preliminary measurement. The counter electrode 28 for preliminary measurement is connected to a lead (not shown). An end of the lead is exposed to outside of the chip 200c at the end portion of the insulating substrate 201 not covered with the spacer 202 and the cover 203.

<Sensor Chip D for Measuring Analyte Concentration>

Figure 34:
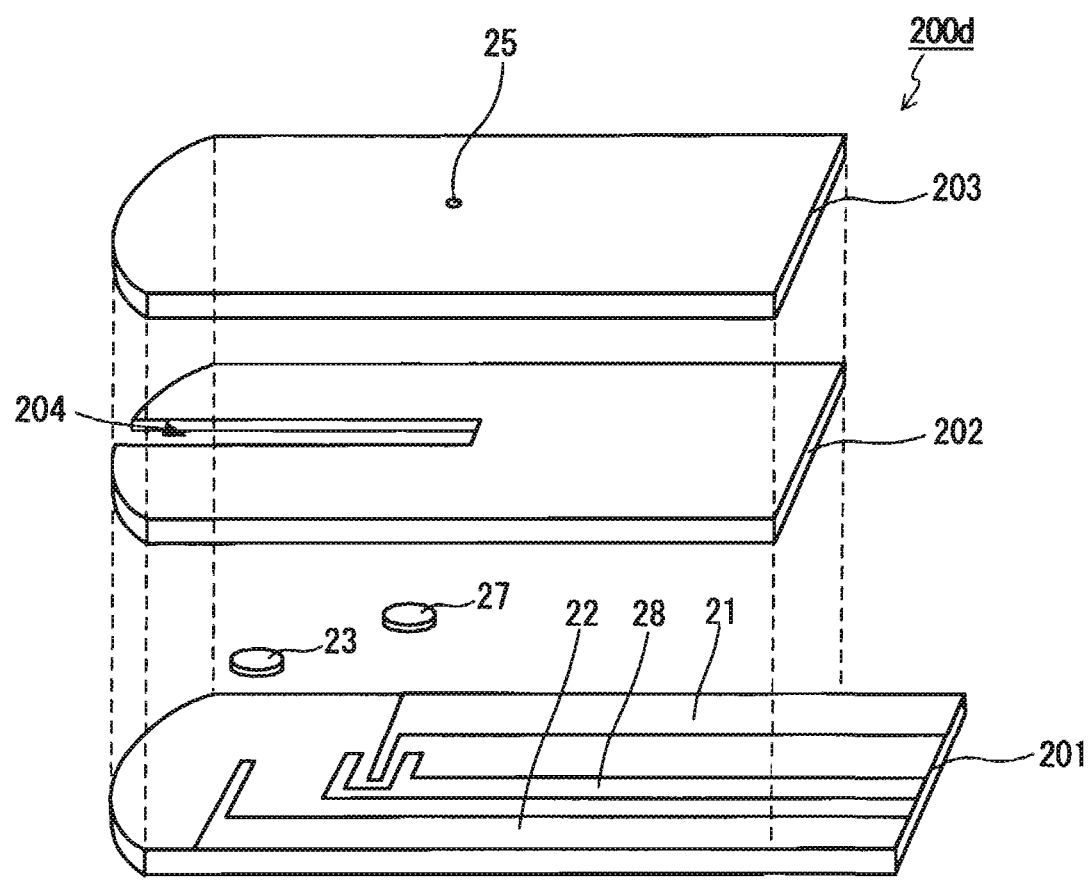
FIG. 34 is an exploded perspective view showing another example of a sensor chip for measuring an analyte concentration of the present invention.
Figure 35:
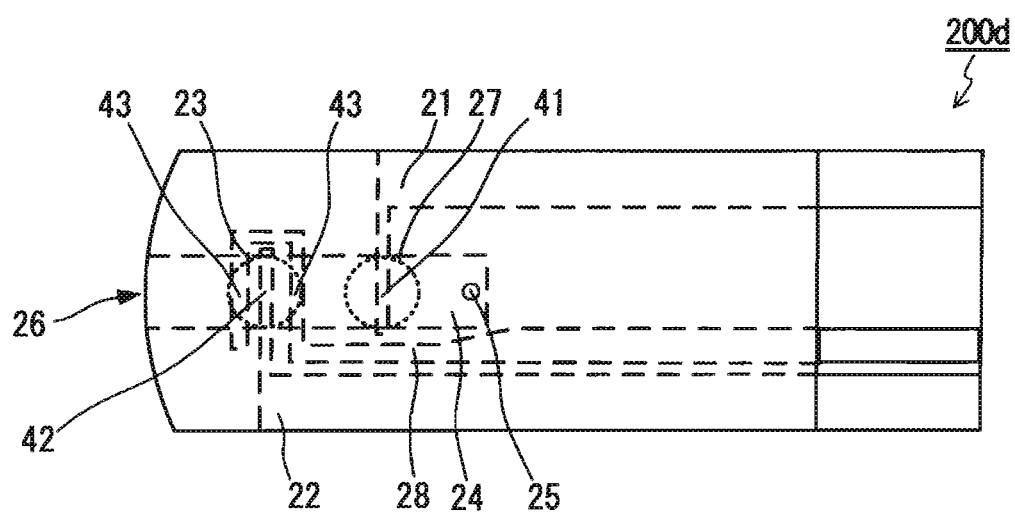
FIG. 35 is a plan view showing another example of a sensor chip for measuring an analyte concentration of the present invention.

FIG. 34 is an exploded perspective view of a sensor chip D for measuring an analyte concentration, and FIG. 35 is a plan view of the sensor chip shown in FIG. 34. As shown in the figures, a sensor chip D200d for measuring an analyte concentration has the same configuration as the sensor chip C for measuring an analyte concentration except that the counter electrode 22 and the working electrode 21 are disposed on the insulating substrate 201 such that the portion 42 of the counter electrode 22 is closer to the blood sample inlet 26 than the portion 41 of the working electrode 21 is, and that the first reagent 23 and the second reagent 27 are disposed to cover the portion 42 of the counter electrode 22 and the portion 41 of the working electrode 21, respectively.

The measurement of the analyte concentration in the blood sample by the sensor chip for measuring an analyte concentration can be performed using, for example, a sensor unit for measuring an analyte concentration, which is another example of a sensor unit of the present invention.

The sensor unit for measuring an analyte concentration includes a sensor chip for measuring an analyte concentration, and a sensor main body detachably provided with the sensor chip. The sensor main body has the same configuration as the sensor main body of the sensor unit for measuring a Hct value shown in FIG. 26 except that a circuit for the preliminary measurement of the analyte concentration in the blood sample is provided in addition to the circuit for measuring a Hct value.

Figure 36:
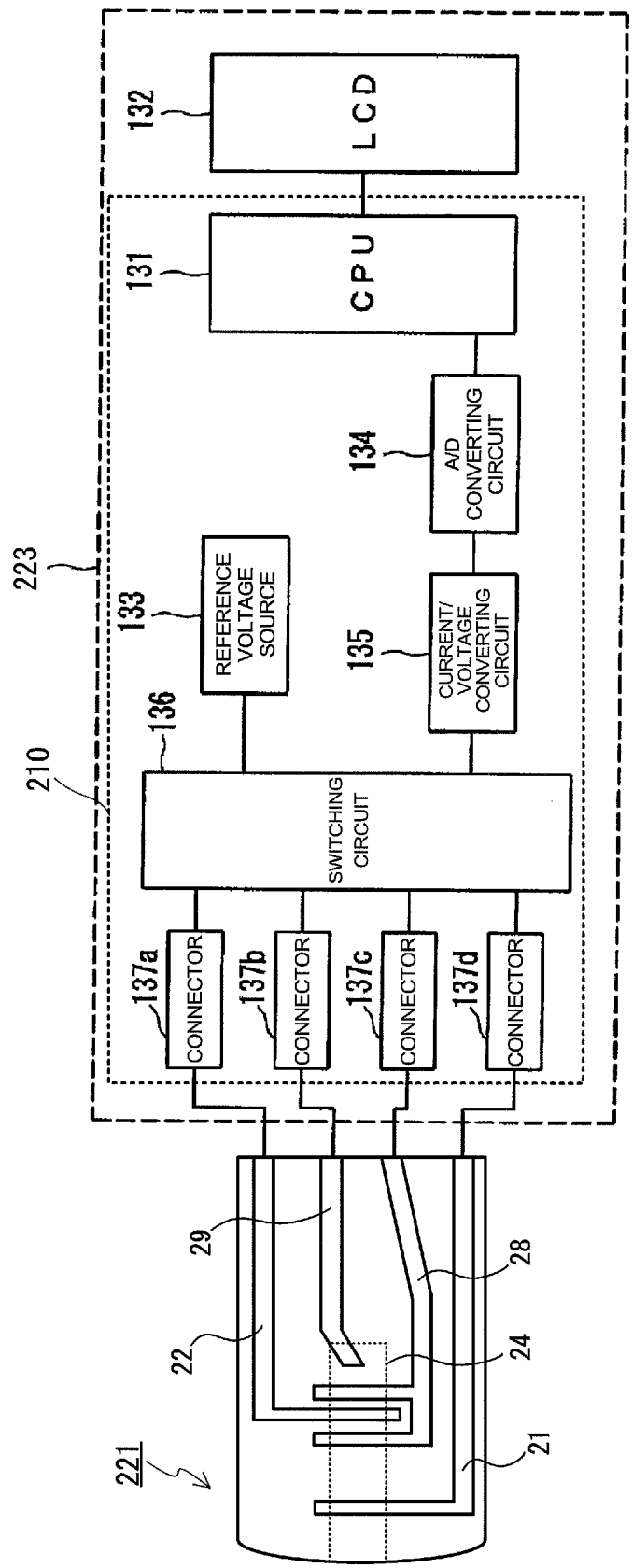
FIG. 36 is a diagram showing an example of a circuit structure of a sensor unit for measuring an analyte concentration of the present invention.

FIG. 36 is a diagram showing an exemplary circuit structure for measuring an analyte concentration in a blood sample, in the sensor unit for measuring an analyte concentration. A sensor main body 223 includes: a voltage applying circuit 210 for applying a voltage across at least two of the electrodes selected from the working electrode 21 for correction, the counter electrode 22 for correction, the counter electrode 28 for preliminary measurement, and the blood sample detecting electrode 29 in the sensor chip 221 for measuring an analyte concentration; and a liquid crystal display (LCD) 132 as a display section of the sensor main body. The voltage applying circuit 210 is capable of applying a predetermined voltage across the working electrode 21 for correction and the counter electrode 22 for correction, and switching the applied potential to the electrodes so that the electrode can be used as the anode or cathode. By the switching, the counter electrode 22 for correction also can serve as the working electrode for preliminary measurement. The voltage applying circuit 210 includes four connectors 137a, 137b, 137c, and 137d, a switching circuit 136, a current/voltage converting circuit 135, an A/D converting circuit 134, a reference voltage source 133, and a central processing unit (CPU) 131. These elements 131, 132, 133, 134, 135, 136, 137a, 137b, 137c, and 137d are connected electrically to one another, as indicated by the solid lines in FIG. 36.

The measurement of the analyte concentration in the blood sample using the sensor unit for measuring an analyte concentration is performed as follows, for example.

First, under an instruction from the CPU 131, the working electrode 21 for correction is connected to the current/voltage converting circuit 135 via the connector 137d, and the blood sample detecting electrode 29 is connected to the reference voltage source 133 via the connector 137b. This is followed by application of a certain voltage across the electrodes under an instruction from the CPU 131. The applied voltage may be, for example, 0.05 V to 1 V, when the working electrode for correction is the anode and the blood sample detecting electrode is the cathode. Introducing a blood sample into the blood sample holder 24 of the sensor chip 221 through the blood sample inlet of the sensor chip 221 generates a current flow between the working electrode 21 for correction and the blood sample detecting electrode 29. The current value is converted into a voltage value by the current/voltage converting circuit 135, and is sent to the CPU 131 after conversion into a digital value by the A/D converting circuit 134. Based on the digital value, the CPU 131 detects the inflow of the blood sample into the blood sample holder.

Following the inflow of the blood sample, the analyte in the blood sample is allowed to react with the redox enzyme for, for example, 0 to 60 seconds, so as to calculate a preliminary measurement concentration of the analyte in the blood sample as follows. First, under an instruction from the CPU 131, the switching circuit 136 comes into operation to connect the counter electrode for preliminary measurement, also serving as the counter electrode 22 for correction, to the current/voltage converting circuit 135 via the connector 137a, and the working electrode 28 for preliminary measurement to the reference voltage source 133 via the connector 137c. This is followed by application of a voltage of the foregoing range across the electrodes, under an instruction from the CPU 131. For example, when the working electrode for preliminary measurement is the anode and the counter electrode for preliminary measurement is the cathode, a preliminary measuring voltage of 0.05 to 1 V is applied. The preliminary measuring voltage is applied for an adjusted time period of, for example, 0.01 to 30 seconds. The value of the current flowing between the electrodes by the application of the preliminary measuring voltage is converted into a voltage value by the current/voltage converting circuit 135, and is sent to the CPU 131 after conversion into a digital value by the A/D converting circuit 134. Based on the digital value, the CPU 131 calculates a preliminary measurement concentration of the analyte. The preliminary measurement concentration is calculated by referring to a standard curve or a standard table, relating the preliminary measurement concentration of the analyte to the amount of current after a predetermined time period from the application of the preliminary measuring voltage.

After calculating the preliminary measurement concentration, the Hct value of the blood sample is calculated as follows, for example. First, under an instruction from the CPU 131, the switching circuit 136 comes into operation to connect the working electrode 21 for correction to the current/voltage converting circuit 135 via the connector 137d, and the counter electrode 22 for correction to the reference voltage source 133 via the connector 137a. This is followed by application of a Hct value measuring voltage of 3.0 V or less across the electrodes under an instruction from the CPU 131, when the working electrode for correction is the anode and the counter electrode for correction is the cathode. The Hct value measuring voltage is applied for an adjusted time period of, for example, 0.001 to 60 seconds. The value of the current flowing between the electrodes by the application of the Hct value measuring voltage is converted into a voltage value by the current/voltage converting circuit 135, and is sent to the CPU 131 after conversion into a digital value by the A/D converting circuit 134. Based on the digital value, the CPU 131 calculates an Hct value. The Hct value is calculated by referring to, for example, a standard curve or a standard table, relating Hct value to the amount of current after a predetermined time period from the application of the Hct value measuring voltage.

Then, in the CPU 131, the preliminary measurement concentration calculated as above is corrected based on the Hct value, so as to determine the analyte concentration in the blood sample. The resulting analyte concentration is displayed visually on the LCD 132. The correction of the preliminary measurement concentration based on the Hct value is performed by referring to, for example, a standard curve or a standard table, relating the analyte concentration in the blood sample to Hct value and preliminary measurement concentration.

The following will describe the present invention by way of examples and comparative examples.

EXAMPLE 1

A sensor chip A for measuring a Hct value was prepared. Palladium was used as the electrode cores of the working electrode and the counter electrode. Using a spacer having a thickness of 100 μm, a 0.8 microliter (μL)-volume blood sample holder was formed. The effective areas of the working electrode and the counter electrode in the blood sample holder were 0.4 mm² and 0.7 mm², respectively, and the closest distance between the working electrode and the counter electrode was 2.4 mm. A reaction reagent layer A containing the reductant but not the oxidant of the redox substance was disposed to cover the surface of the working electrode facing the blood sample holder. A reaction reagent layer B containing the oxidant but not the reductant of the redox substance was disposed to cover the surface of the counter electrode facing the blood sample holder. The reaction reagent layer A was disposed on the surface by applying a reagent solution, prepared by dissolving 50 mM potassium ferrocyanide (KANTO CHEMICAL CO., INC.) and 250 U/g of glucose oxidase (SIGMA) in a 0.5 mass % CMC aqueous solution (DAIICHI KOGYO CO., LTD.), on the surface of the electrode core of the working electrode (0.63 mg/sensor), and then by drying the solution at 55° C. for 10 minutes. The reaction reagent layer B was disposed on the surface by applying a reagent solution, prepared by dissolving 50 mM potassium ferricyanide (KANTO CHEMICAL CO., INC.) and 250 U/g of glucose oxidase (SIGMA) in a 0.5 mass % CMC aqueous solution, on the surface of the electrode core of the counter electrode (0.63 mg/sensor), and then by drying the solution at 55° C. for 10 minutes. The cover had been rendered hydrophilic in advance using a surfactant. The closest distance between the working electrode and the reaction reagent layer B was 1.8 mm.

Three kinds of blood samples with the Hct values of 25%, 45%, and 65% were prepared. Each blood sample was introduced into the blood sample holder of the sensor chip, and a voltage of 3.0 V or less was applied across the working electrode and the counter electrode serving as the anode and the cathode, respectively. A resulting current (response current) flowing between the working electrode and the counter electrode was measured. The results of measurement of response current are represented by the graphs shown in FIGS. 7 through 13. In each figure, graph (A) represents changes in response current value (μA) of each blood sample as a function of time. Graph (B) represents changes in relative amplitude values of the response currents obtained from the 25% and 65% Hct blood samples (sensitivity difference (%)) relative to the amplitude of the response current obtained from the 45% Hct blood sample, as a function of time. In graph (A) and graph (B), the horizontal axis represents time from the voltage application in seconds (sec).

As shown in the graphs, the sensor chip of Example 1 was able to detect response currents reflecting the Hct values of the blood samples with a stable and distinct sensitivity difference, immediately after the application of a voltage of 3.0 V or less across the working electrode and the counter electrode serving as the anode and the cathode, respectively.

EXAMPLE 2

A sensor chip was prepared as in Example 1 except that the reaction reagent layer A was prepared using a regent solution that had been prepared by dissolving 50 mM potassium ferrocyanide and 1.0 mass % bovine serum albumin (SIGMA) in a 0.5 mass % CMC aqueous solution.

Each of the three kinds of blood samples was introduced into the blood sample holder of the sensor chip, and a voltage of 3.0 V or less was applied across the working electrode and the counter electrode serving as the anode and the cathode, respectively. A resulting response current flown between the working electrode and the counter electrode was measured. The results of measurement of response current are represented by the graphs shown in FIGS. 14 through 19. As shown in the graphs, the sensor chip of Example 2 was able to detect response currents reflecting the Hct values of the blood samples with a stable and distinct sensitivity difference, immediately after the application of a voltage of 3.0 V or less across the working electrode and the counter electrode serving as the anode and the cathode, respectively.

COMPARATIVE EXAMPLE 1

A sensor chip was prepared as in Example 1, except that the reaction reagent layer A was not disposed.

Figure 20:
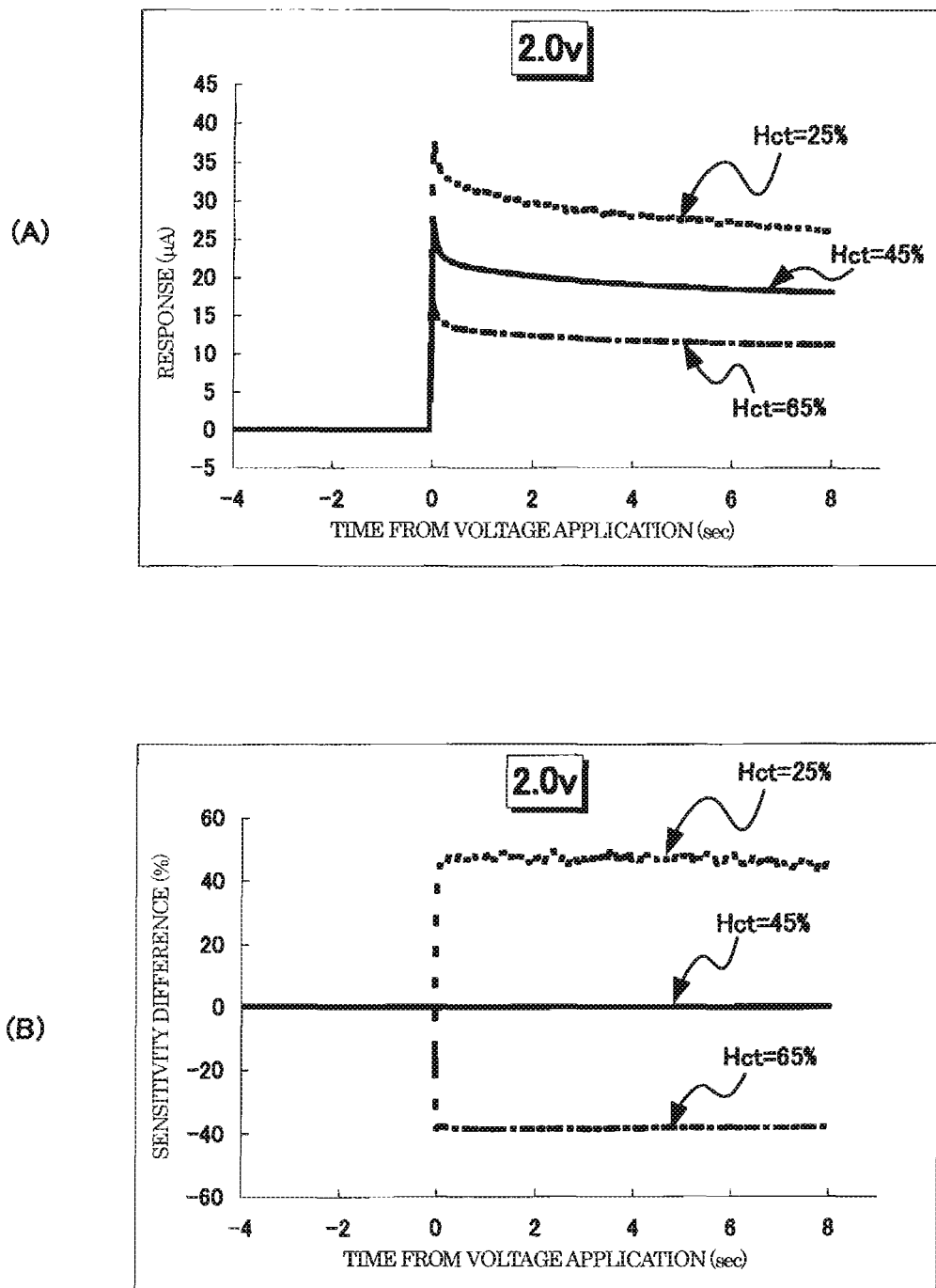
FIG. 20 is a graph representing an example of measurement results of Hct value by a sensor chip of Comparative Example 1.
Figure 21:
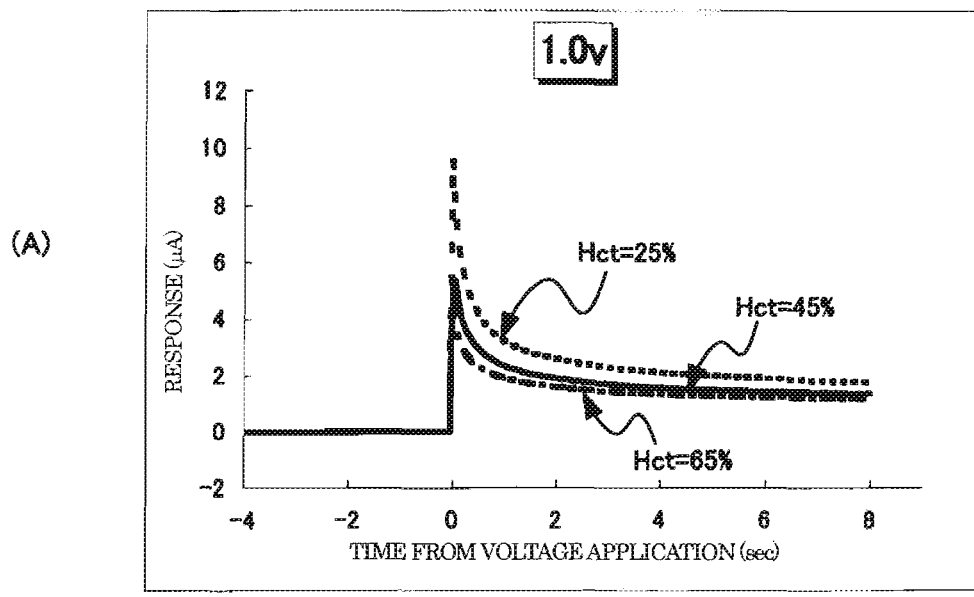
FIG. 21 is a graph representing another example of measurement results of Hct value by the sensor chip of Comparative Example 1.
Figure 21:
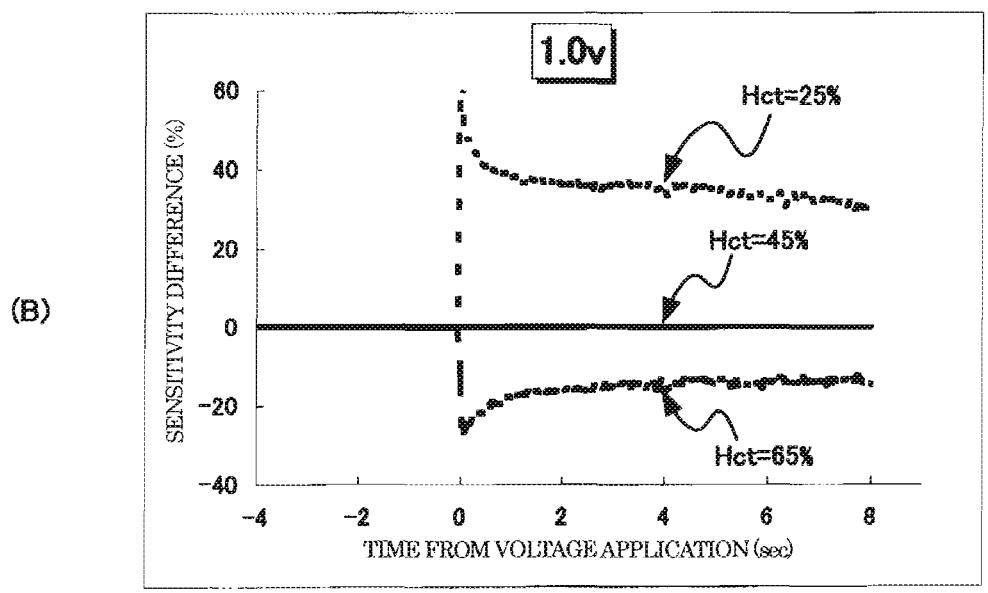
Figure 22:
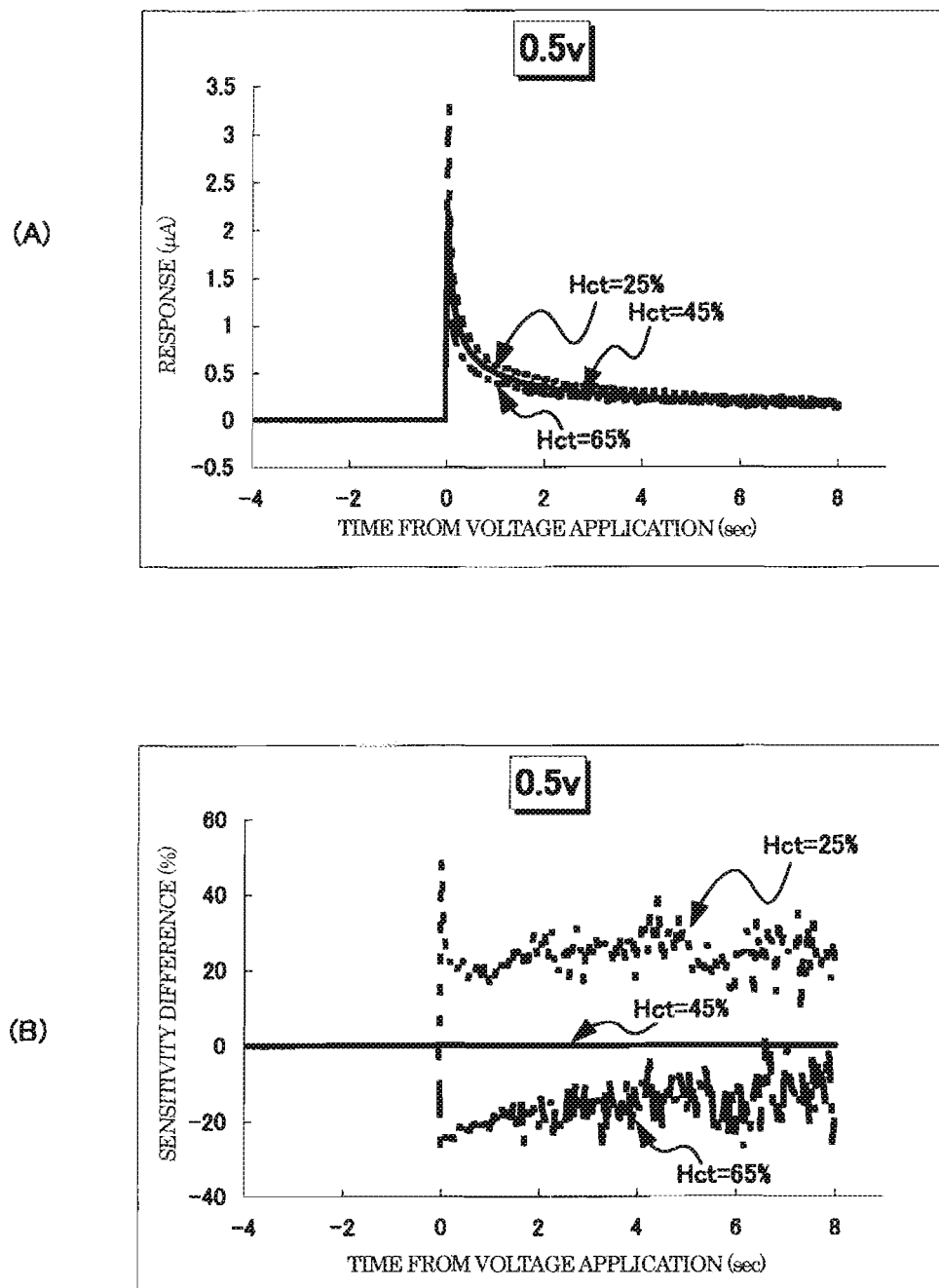
FIG. 22 is a graph representing another example of measurement results of Hct value by the sensor chip of Comparative Example 1.

Each of the three kinds of blood samples was introduced into the blood sample holder of the sensor chip, and voltages of 2.0 V, 1.0 V, and 0.5 V were applied across the working electrode and the counter electrode serving as the anode and the cathode, respectively. A resulting response current flown between the working electrode and the counter electrode was measured. The results of measurement of response current are represented by the graphs shown in FIGS. 20 through 22. As shown in FIGS. 21 and 22, a stable sensitivity difference was not obtained in the sensor chip of Comparative Example 1 when a voltage of 1.0 V or less was applied across the working electrode and the counter electrode serving as the anode and the cathode, respectively. More specifically, as shown in FIG.

21, when a voltage of 1.0 V was applied across the working electrode and the counter electrode serving as the anode and the cathode, respectively, the sensitivity difference fluctuated abruptly immediately after the voltage application, and, though the fluctuations gradually leveled off, the sensitivity difference did not return to the normal state after three seconds from the voltage application. Further, as shown in FIG. 22, when a voltage of 0.5 V was applied across the working electrode and the counter electrode serving as the anode and the cathode, respectively, the sensitivity difference fluctuated abruptly immediately after the voltage application and continued fluctuating over a wide range. The sensitivity difference did not return to the normal state after three seconds from the voltage application.

Though the reasons for these undesirable outcomes from the sensor chip of Comparative Example 1 are unclear, it appears that the results are due to the redox current, generated by the electrolysis of water in the blood component, accounting for the majority of the redox current on the working electrode.

COMPARATIVE EXAMPLE 2

A sensor chip was prepared that had the same configuration as the sensor chip C for measuring a Hct value, except that a reaction reagent layer C containing the reductant and the oxidant was disposed to cover the surface of each of the working electrode and the counter electrode facing the blood sample holder, instead of the first reagent and the second reagent. Palladium was used as the electrode cores of the working electrode and the counter electrode. Using a spacer having a thickness of 100 μm, a 304 nanoliter-volume blood sample holder was formed. The effective areas of the working electrode and the counter electrode in the blood sample holder were 0.32 $mm^2$ and 0.4 $mm^2$, respectively, and the closest distance between the working electrode and the counter electrode was 0.05 mm. The reaction reagent layer C was disposed on the surface by applying a reagent solution, prepared by dissolving 60 mM potassium ferricyanide, 8.25 mM potassium ferrocyanide, 1.0 mass % taurine (nacalai tesque), and 0.25 mass % maltitol (HAYASHIBARA) in a 0.1 mass % CMC aqueous solution, on the surface of the electrode core of each electrode (0.55 mg/sensor), and then by drying the solution at 20° C. for 50 minutes.

Figure 23:
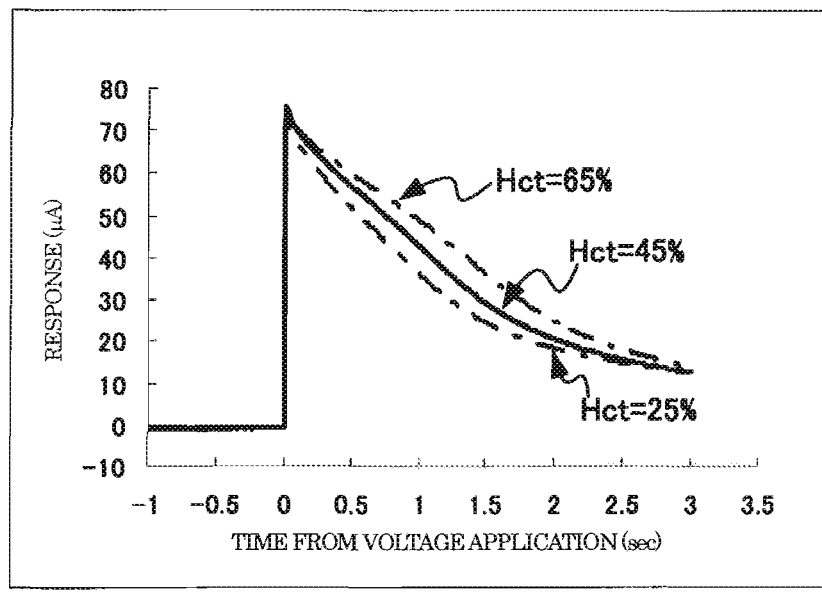
FIG. 23 is a graph representing an example of measurement results of Hct value by a sensor chip of Comparative Example 2.
Figure 23:
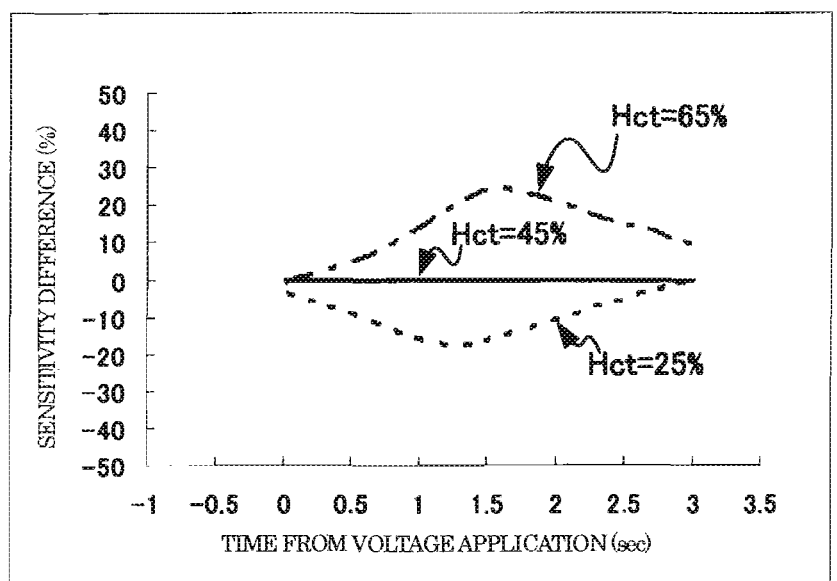

Each of the three kinds of blood samples was introduced into the blood sample holder of the sensor chip, and a voltage of 0.2 V was applied across the working electrode and the counter electrode serving as the anode and the cathode, respectively. A resulting response current flowing between the working electrode and the counter electrode was measured. The results of measurement of response current are represented by the graph shown in FIG. 23. As shown in the graph, in the sensor chip of Comparative Example 2, the sensitivity difference was small immediately after the application of a voltage of 0.2 V across the working electrode and the counter electrode serving as the anode and the cathode, respectively. Further, the sensitivity difference was unstable throughout the measurement.

COMPARATIVE EXAMPLE 3

A sensor chip was prepared as in Comparative Example 2 except that a reaction reagent layer D containing the oxidant but not the reductant was disposed instead of the reaction reagent layer C. The reaction reagent layer D was disposed on the surface by applying a reagent solution, prepared by dissolving 60 mM potassium ferricyanide, 1.0 mass % taurine, and 0.25 mass % maltitol in a 0.1 mass % CMC aqueous solution, on the surface of the electrode core of each electrode (0.55 mg/sensor), and then by drying the solution at 20° C. for 50 minutes.

Figure 24:
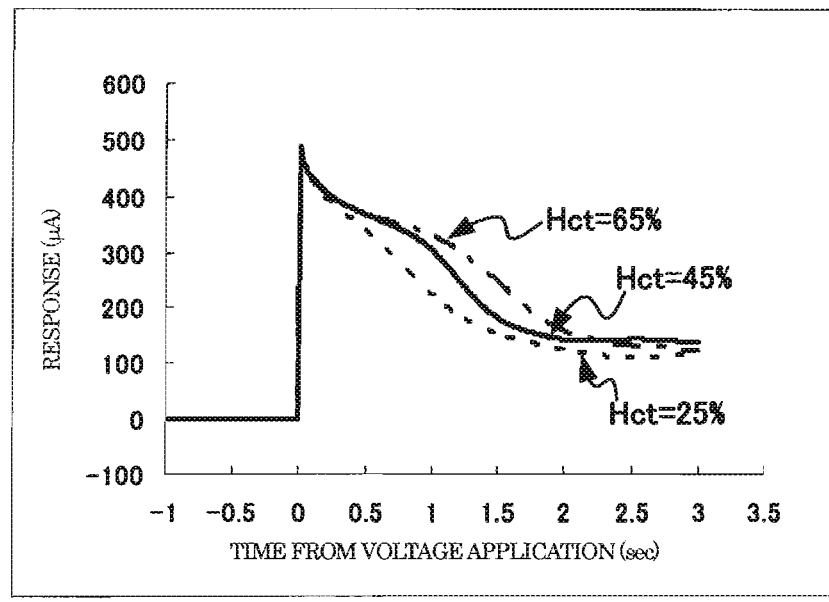
FIG. 24 is a graph representing an example of measurement results of Hct value by a sensor chip of Comparative Example 3.
Figure 24:
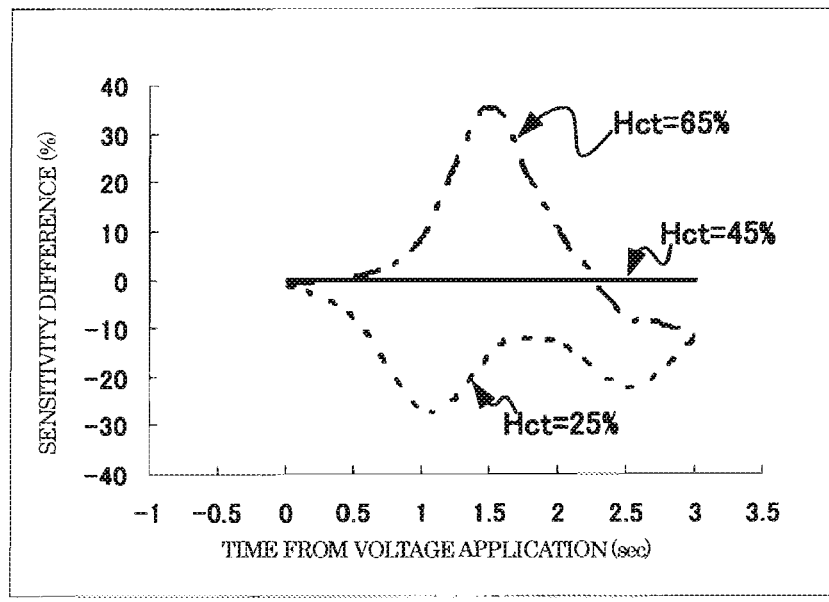

Each of the three kinds of blood samples was introduced into the blood sample holder of the sensor chip, and a voltage of 2.5 V was applied across the working electrode and the counter electrode serving as the anode and the cathode, respectively. A resulting response current flowing between the working electrode and the counter electrode was measured. The results of measurement of response current are represented by the graph shown in FIG. 24. As shown in the graph, in the sensor chip of Comparative Example 3, the sensitivity difference was small immediately after the voltage application, even with the application of a relatively high voltage of 2.5 V across the working electrode and the counter electrode serving as the anode and the cathode, respectively. Further, the sensitivity difference was unstable throughout the measurement.

COMPARATIVE EXAMPLE 4

A sensor chip was prepared as in Comparative Example 2 except that: instead of the reaction reagent layer C, a reaction reagent layer E containing the reductant but not the oxidant was disposed to cover the surface of the counter electrode facing the blood sample holder; neither the reaction reagent layer C nor the reaction reagent layer E was disposed to cover the surface of the working electrode facing the blood sample holder; a CMC film was disposed on the surface of the electrode core of the working electrode; and the effective areas of the working electrode and the counter electrode in the blood sample holder were 0.4 $mm^2$ and 0.5 $mm^2$, respectively. The CMC film was disposed on the surface of the electrode core of the working electrode by dropping 0.01 to 100 mg of 0.01 to 2.0 mass % CMC aqueous solution and then drying it. The reaction reagent layer E was disposed on the surface by applying a reagent solution, prepared by dissolving 60 mM potassium ferrocyanide, 1.0 mass % taurine, and 0.25 mass % maltitol in a 0.1 mass % CMC aqueous solution, on the surface of the electrode core of the counter electrode (0.55 mg/sensor), and then by drying the solution at 20° C. for 50 minutes.

Figure 25:
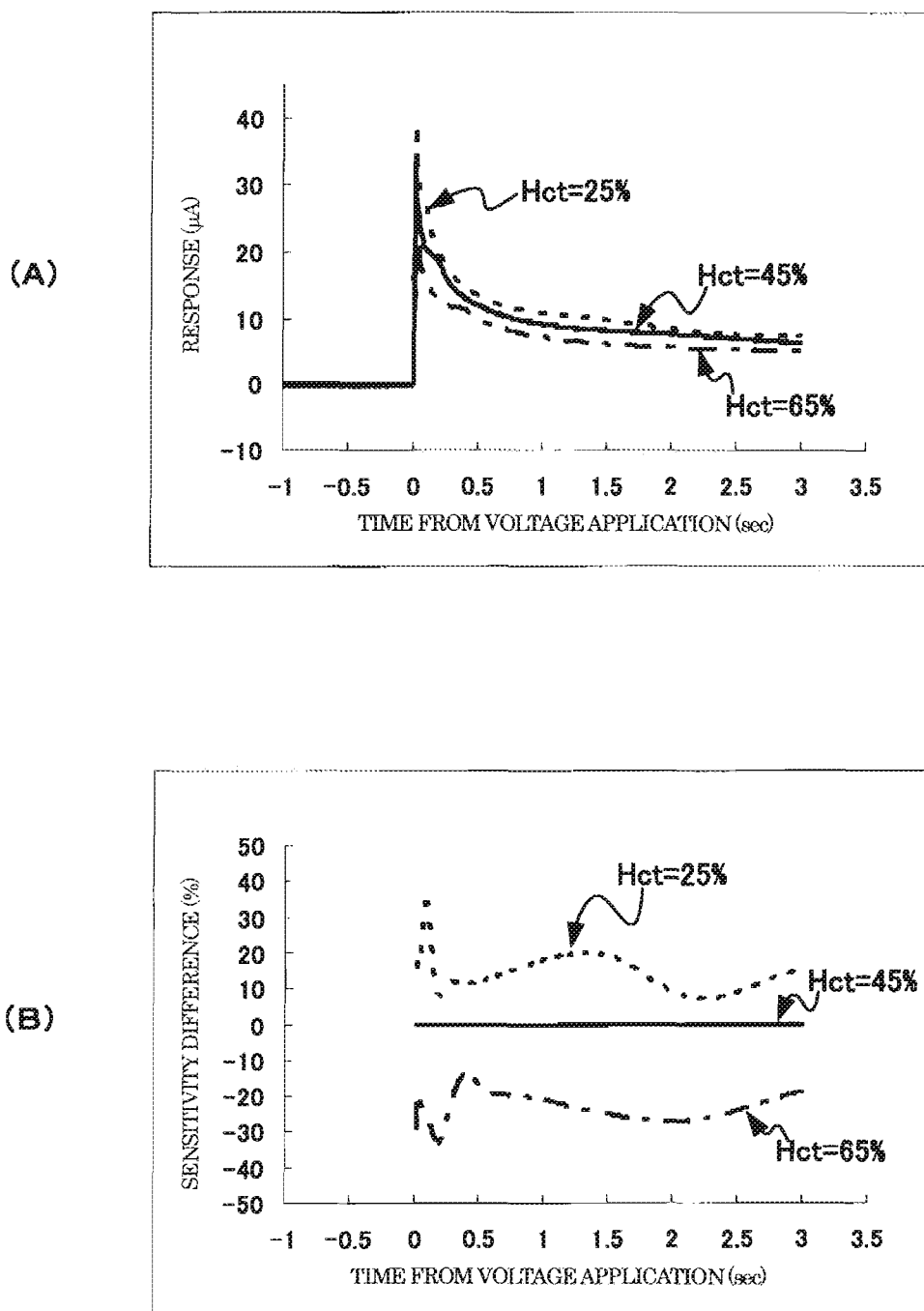
FIG. 25 is a graph representing an example of measurement results of Hct value by a sensor chip of Comparative Example 4.

Each of the three kinds of blood samples was introduced into the blood sample holder of the sensor chip, and a voltage of 2.5 V was applied across the working electrode and the counter electrode serving as the anode and the cathode, respectively. A resulting response current flowing between the working electrode and the counter electrode was measured. The results of measurement of response current are represented by the graph shown in FIG. 25. As shown in the graph, in the sensor chip of Comparative Example 4, the sensitivity difference was unstable throughout the measurement, even with the application of a relatively high voltage of 2.5 V across the working electrode and the counter electrode serving as the anode and the cathode, respectively.

Separately, measurements of response current were made as in Examples 1 and 2 and Comparative Examples 1 through 4, using sensor chips (1) to (6) for measuring an analyte concentration (described below), and three kinds of blood samples with 25%, 45%, and 65% Hct values, each containing 67 mg/dl of glucose. The results were similar to those obtained in the measurements of response current shown in FIGS. 7 through 25. Further, a measurement of glucose concentration in the blood sample using the sensor chips (1) and (2) for measuring an analyte concentration yielded an accurate result.

The sensor chips (1) through (3) for measuring an analyte concentration had the same configurations as the sensor chips of Examples 1 and 2 and Comparative Example 1, respectively, except that, in the blood sample holder, a counter electrode for preliminary measurement having an effective area of 0.4 mm$^2$ was formed to provide a closest distance of 1.8 mm between the counter electrode and the counter electrode for preliminary measurement. The sensor chips (4) through (6) for measuring an analyte concentration had the same configurations as the sensor chips of Comparative Examples 2 through 4, respectively, except that, in the blood sample holder, a counter electrode for preliminary measurement having an effective area of 0.7 mm$^2$ was formed to provide a closest distance of 0.05 mm between the counter electrode and the counter electrode for preliminary measurement, and that the closest distance between the working electrode and the counter electrode was 0.7 mm.

INDUSTRIAL APPLICABILITY

The present invention provides a method for measuring a Hct value of a blood sample, a method for measuring a concentration of an analyte in a blood sample, and a sensor chip and a sensor unit suited for such measurements, that are capable of stably measuring a Hct value of a blood sample with sufficient detection sensitivity even with a small Hct value measuring voltage.

The invention claimed is:

1. A sensor chip for electrochemically measuring a concentration of an analyte in a blood sample, comprising:
   a substrate,
   a preliminary measurement analyzer and a hematocrit value analyzer disposed on the substrate,
   the preliminary measurement analyzer comprising a preliminary working electrode and a preliminary counter electrode,
   the hematocrit value analyzer comprising a working electrode and a counter electrode,
   wherein a first reagent containing an oxidant of a redox substance is disposed to cover the surface of the preliminary measurement analyzer and the counter electrode,
   a second reagent containing a reductant of a redox substance is disposed to cover the surface of the working electrode and
   the first reagent and the second reagent are separated from each other on the substrate.

2. The sensor chip according to claim 1, wherein a common electrode is used for the preliminary working electrode and the counter electrode.

3. A sensor chip for electrochemically measuring a concentration of an analyte in a blood sample, comprising:
   a substrate,
   a preliminary measurement analyzer and a hematocrit value analyzer disposed on the substrate,
   the preliminary measurement analyzer comprising a preliminary working electrode and a preliminary counter electrode,
   the hematocrit value analyzer comprising a working electrode and a counter electrode,
   wherein a first reagent containing an oxidant of a redox substance is disposed to cover the surface of the preliminary counter electrode and the counter electrode
   a second reagent containing a reductant of a redox substance is disposed to cover the surface of the working electrode and
   the first reagent and the second reagent are separated from each other on the substrate.

4. The sensor chip according to claim 3, wherein a common electrode is used for the preliminary working electrode and the counter electrode.

* * * * *